(12) United States Patent
Chen et al.

(10) Patent No.: US 10,507,233 B2
(45) Date of Patent: *Dec. 17, 2019

(54) UNIVERSAL N-GLYCAN BINDING REAGENT

(71) Applicant: New England Biolabs, Inc., Ipswich, MA (US)

(72) Inventors: Minyong Chen, Ipswich, MA (US); Xiaofeng Shi, Beverly, MA (US); James C. Samuelson, Newburyport, MA (US); Christopher H. Taron, Essex, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/105,027

(22) Filed: Aug. 20, 2018

(65) Prior Publication Data

US 2019/0008934 A1 Jan. 10, 2019

Related U.S. Application Data

(63) Continuation of application No. 15/320,911, filed as application No. PCT/US2015/037960 on Jun. 26, 2015, now Pat. No. 10,080,787.

(60) Provisional application No. 62/020,335, filed on Jul. 2, 2014.

(51) Int. Cl.
| C12N 9/96 | (2006.01) |
| C12N 9/00 | (2006.01) |
| A61K 38/53 | (2006.01) |
| C12N 9/04 | (2006.01) |
| C12N 9/10 | (2006.01) |
| C07H 21/04 | (2006.01) |

(52) U.S. Cl.
CPC ............ A61K 38/53 (2013.01); C12N 9/0006 (2013.01); C12N 9/1007 (2013.01); C12N 9/93 (2013.01); C12N 9/96 (2013.01); C12Y 201/01063 (2013.01); C12Y 603/02019 (2013.01); *C07K 2319/00* (2013.01)

(58) Field of Classification Search
CPC .............. C12N 9/93; C12Y 101/01027; C12Y 603/02019
USPC .............................. 435/183, 4, 155, 6.11, 7.9
See application file for complete search history.

(56) References Cited

U.S. PATENT DOCUMENTS

| 5,496,714 | A | 3/1996 | Comb et al. |
| 5,643,758 | A | 7/1997 | Guan et al. |
| 5,834,247 | A | 11/1998 | Comb et al. |
| 6,521,425 | B2 | 2/2003 | Perler et al. |
| 6,849,428 | B1 | 2/2005 | Evans et al. |
| 6,858,775 | B1 | 2/2005 | Xu et al. |
| 6,897,285 | B2 | 5/2005 | Xu et al. |
| 6,984,505 | B2 | 1/2006 | Xu et al. |
| 6,987,007 | B2 | 1/2006 | Xu et al. |
| 7,001,745 | B1 | 2/2006 | Xu et al. |
| 7,060,465 | B2 | 6/2006 | Xu et al. |
| 7,157,224 | B2 | 1/2007 | Perler et al. |
| 7,271,256 | B2 | 9/2007 | Evans et al. |
| 7,799,524 | B2 | 9/2010 | Kindermann et al. |
| 7,825,218 | B2 | 11/2010 | Riggs et al. |
| 7,883,867 | B1 | 2/2011 | Riggs et al. |
| 7,888,090 | B2 | 2/2011 | Barnikow et al. |
| 7,939,284 | B2 | 5/2011 | Johnsson et al. |
| 8,163,479 | B2 | 4/2012 | Jaccard et al. |
| 8,178,314 | B2 | 5/2012 | Kindermann et al. |
| 8,227,602 | B2 | 7/2012 | Gautier et al. |
| 8,367,361 | B2 | 2/2013 | Johnsson et al. |
| 8,623,615 | B2 | 1/2014 | Riggs et al. |
| 8,623,627 | B2 | 1/2014 | Gautier et al. |

OTHER PUBLICATIONS

Zhang, et al., Nat. Biotechnol., 21, 660-666 (2003).
Nilsson, et al., Nature Methods, 6, 809-813 (2009).
Chen, et al., Analyst, 139, 688 (2014).
Larsen, et al., Mol. Cell. Proteomics, 6, 1778-1787 (2007).
Ahn, et al., Anal. Chem., 82, 4441-4447 (2010).
Fanayan, et al., Electrophoresis,33,1746-1754 (2012).
Ruhaak, et al., Anal Bioanal Chem. 397, 8, 3457-3481 (2010).
Kalay, et al., Anal Biochem., 423, 1,153-62 (2012).
Radoslaw, et al., Analytical Biochemistry, 486, 38-40 (2015).
Deeb, et al., Mol Cell Proteomics, 1, 240-51 (2014).
Altschul, et al., Nuc. Ac. Res. 25, 3389-3402 (1997).
Pearson, et al., PNAS 85, 8, 2444-2448 (1988).
Speight, et al., Chemistry & Biology, 8, 951-965 (2001).
Niture, et al., Biochemical and Biophysical Research Communications, 337, 4, 2005.
Wen, et al., Cell Cycle, 9, 22, 4506-4517, 2010.
Yoshida, et al., Biosci, Biotechnol. Biochem, 77, 11, 2623-2631, 2007.
Yoshida, et al., EMBO Reports, 6, 3, 239-244, 2005.
Yoshida, et al., Nature, 418, 438-442, 2002.
International Searching Authority, International Search Report and Written Opinion for International Application No. PCT/US2015/037960 dated Sep. 9, 2015.
Devos, et al., Proteins: Structure, Function and Genetics, 2000, vol. 41: 98-107.

(Continued)

*Primary Examiner* — Robert B Mondesi
*Assistant Examiner* — Mohammad Y Meah
(74) *Attorney, Agent, or Firm* — New England Biolabs, Inc; Harriet M. Strimpel

(57) ABSTRACT

Methods of capturing N-glycan linked glycomolecules including N-glycans, N-glycopeptides and N-glycoproteins are described. The methods provide substantially unbiased capture of charged and uncharged N-glycans and/or N-glycan linked glycomoleules. Binding reagents for substantially unbiased binding of N-glycans and/or N-glycan linked glycomolecules are also described.

8 Claims, 13 Drawing Sheets

Specification includes a Sequence Listing.

(56) References Cited

OTHER PUBLICATIONS

Whisstock, et al., Quarterly Review of Biophysics, 2003, vol. 36 (3): 307-340.
Witkowski, et al., Biochemistry, 38, 11643-11650, 1999.
Kisselev, Structure, 2002, vol. 10: 8-9.

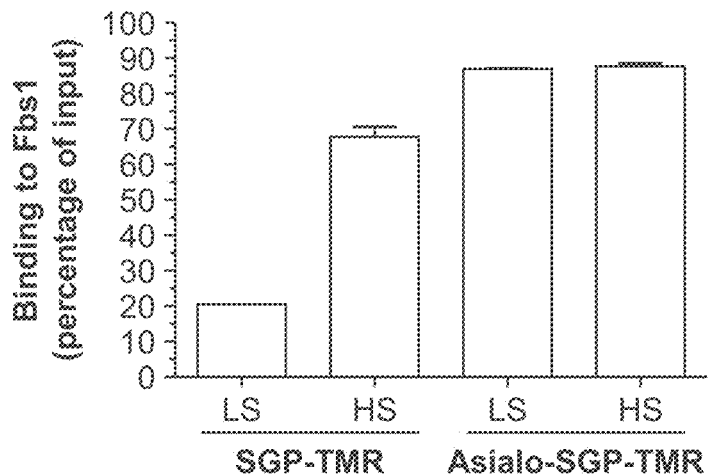
FIG. 6A
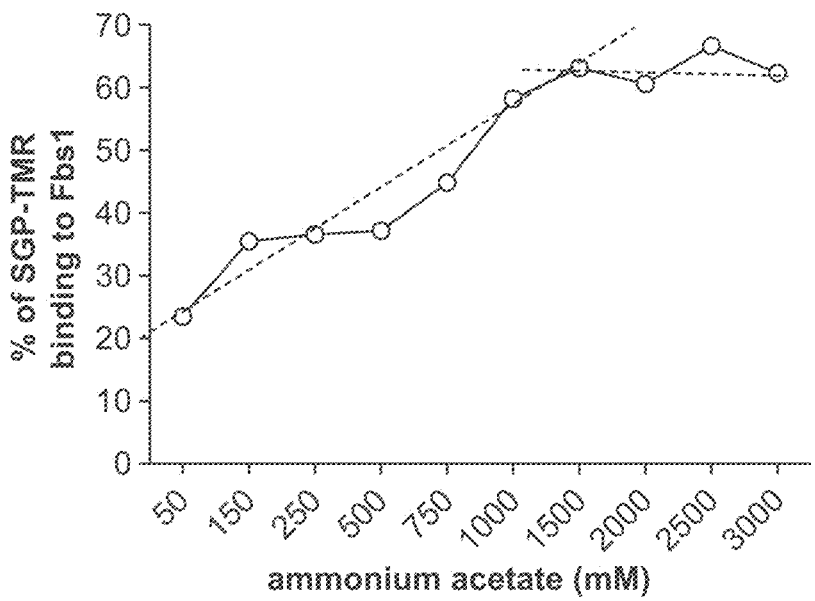
FIG. 6B
| Condition: | Low Salt | High Salt |
|---|---|---|
| Kd (μM): | 3.0 ± 0.12 | 1.43 ± 0.04 |
| Statistic: | n=3, P= 0.0002 | |
FIG. 6C

Amino acid sequence of human Fbs1 SBD:

$F_{113}$YFLSKRRRNLLRNPCGEEDLEG
WCDVEHGGDGWRVEELPGD$_{154}$S$_{155}$G$_{156}$VEFTHDESVKKYFASSF$_{173}$E$_{174}$
WCRKAQVIDLQAEGYWEELLDTTQPAIVVKDWYSGRSDAGCLYELTV
KLLSEHENVLAEFSSGQVAVPQDSDGGGWMEISHTFTDYGPGVRFV
RFEHGGQDSVYWKGWFGARVTNSSVWVEP$_{296}$  (SEQ. ID NO:2)

| | a. a. position | 158 | 159 | 160 | 177 | 178 |
|---|---|---|---|---|---|---|
| mouse Fbs1 | wt | D | N | G | F | E |
| human Fbs1 | a. a. position | 154 | 155 | 156 | 173 | 174 |
| | wt | D | S | G | F | E |
| | S155A | D | A | G | F | E |
| | S155G | D | G | G | F | E |
| | PPG | P | P | G | F | E |
| | PPS | P | P | S | F | E |
| | PPR | P | P | R | F | E |
| | YR | D | S | G | Y | R |
| | S155G+YR | D | G | G | Y | R |
| | PPR+YR | P | P | R | Y | R |

FIG. 9A

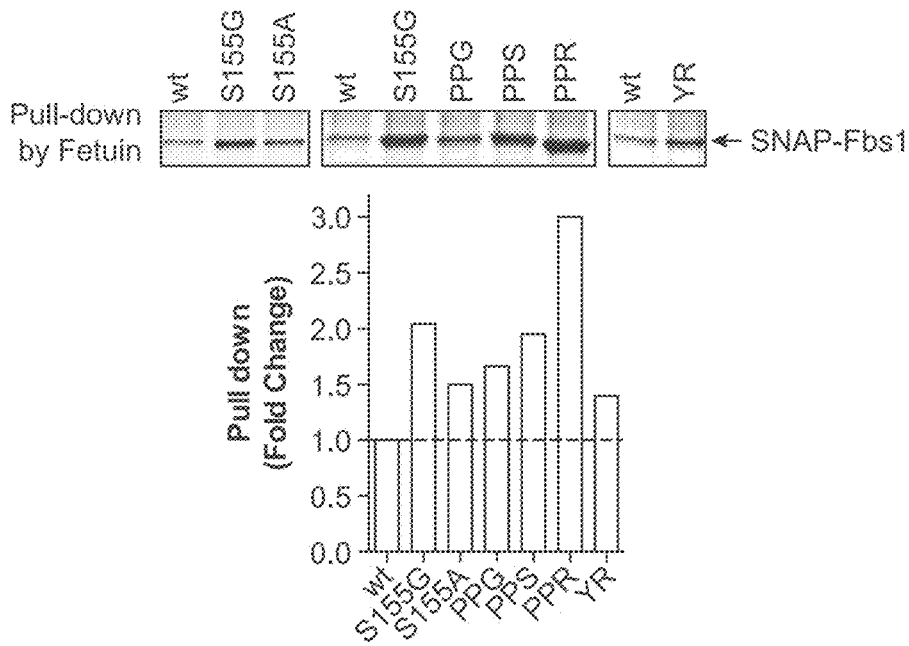

FIG. 9B

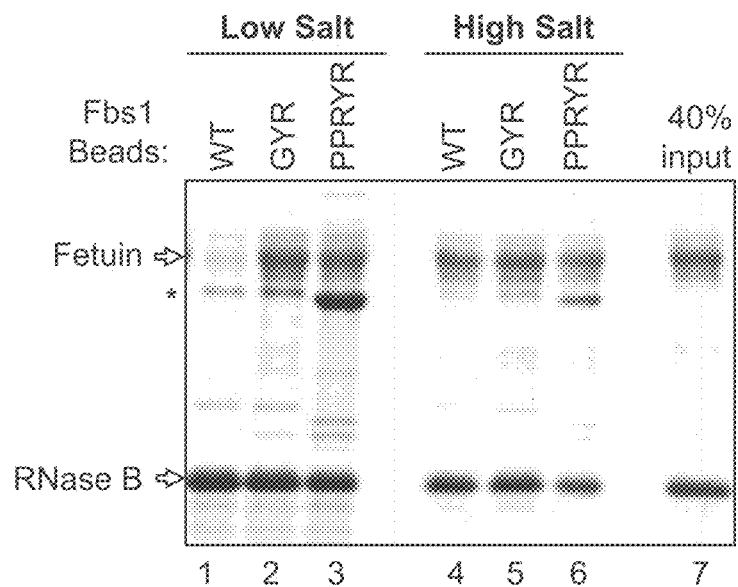
FIG. 10A
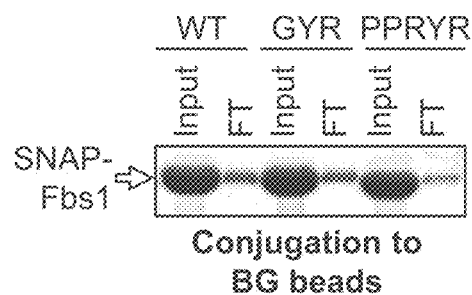
FIG. 10B
|  |  | Fetuin/RNase B |
|---|---|---|
|  | Input | 1 |
| Low Salt | WT | 0.29 |
|  | GYR | 0.98 |
|  | PPRYR | 1.05 |
| High Salt | WT | 0.92 |
|  | GYR | 0.99 |
|  | PPRYR | 1.19 |
FIG. 10C

UNIVERSAL N-GLYCAN BINDING REAGENT

CROSS REFERENCE

This application is a continuation of U.S. application Ser. No. 15/320,911, filed Dec. 21, 2016, which is a § 371 application of International Application No. PCT/US2015/37960 filed Jun. 26, 2015, which claims priority from U.S. Provisional Application No. 62/020,335, filed Jul. 2, 2014, herein incorporated by reference.

BACKGROUND

Glycosylation is one of the most common and structurally diverse forms of protein post-translational modification. Glycans can be N-linked to an asparagine residue, or O-linked to either a serine or a threonine residue. Glycans on any given protein can vary widely in structure, composition and the site of attachment on a protein. Individual sites within one protein type may even contain a heterogeneous population of glycan modifications. This complexity interferes with readily analyzing and characterizing glycosylated proteins. Separating glycans from a glycosylated protein is a common first step in characterizing the glycans present on a glycoprotein. However, this method yields no information about the glycan attachment site on the protein.

Chemical methods exist for capturing glycans, glycopeptides and glycoproteins. For example, hydrazide chemistry (see for example Zhang, et al., *Nat. Biotechnol.*, 21, 660-666 (2003)) involves periodate oxidation of carbohydrate cis-diol groups to dialdehydes and covalent coupling between aldehyde and hydrazide groups to form hydrazine bonds on a solid support. Alternatively, mild periodate treatment can oxidize sialic acids on glycans allowing capture of the oxidized glycoproteins by covalent bonding with hydrazide (see for example, Nilsson, et al., *Nature Methods*, 6, 809-813 (2009)). However, this method is selective for only glycans with sialic acids and the glycans are also chemically altered by the oxidation process. Ideally, glycomolecule composition is analyzed without chemical modification. Boronic acid reacts with cis-diol-containing saccharides or polyols to form five- or six-membered cyclic esters and this property has been exploited to isolate glycoproteins and glycopeptides. Importantly, the covalent linkage is easily reversible in an acidic pH (Chen, et al., *Analyst*, 139, 688 (2014)). However, these aforementioned chemical methods unfortunately do not discriminate between N-linked and O-linked glycomolecules.

In titanium dioxide chromatography enrichment, negatively charged sialic acid residues coordinate with the titanium metal ion (for example Larsen, et al., *Mol. Cell. Proteomics*, 6, 1778-1787 (2007)). However, metal ion affinity chromatography (using titanium, zirconium or silver) is not selective for glycans since negatively charged phosphopeptides or peptides with acidic amino acids, such as glutamic acid and aspartic acid may compete for binding.

HILIC enrichment is a common approach for enriching glycans whereby a water-miscible organic solvent (typically acetonitrile) achieves separation of glycans via a partitioning mechanism. Hydrophilic sugar residues partition into the aqueous phase and are attracted to the hydrophilic groups on a solid support (typically silica or derivatized silica). HILIC materials show broad specificity for glycans but do not discriminate between O-glycan linked and N-glycan linked glycomolecules (Chen, et al., *Analyst*, 139, 688 (2014)).

Finally, lectins are proteins with natural carbohydrate binding properties. Many lectins have been characterized and several have been employed for glycopeptide/glycoprotein enrichment or detection. Lectins recognize the variable region of N-linked glycans and the specificity of a lectin may be quite narrow (L-phytohemagglutinin (L-PHA) for the targeted beta-1,6-branched N-linked glycan (see for example, Ahn, et al., *Anal. Chem.*, 82, 4441-4447 (2010)) or relatively broad in the case of Concanavalin A, which recognizes a high mannose structure. Nevertheless, a diverse set of lectins with selective affinities for specific carbohydrate epitopes has been used to investigate the human glycoproteome. However, to this date no single lectin has been shown to possess sufficient selectivity to analyze the entire N-glycan linked glycoproteome. Another major drawback of existing lectin based enrichment methods is low affinity of most natural lectins for their substrates (Kd ranging from 10 mM to 1 µM, (see for example, Fanayan, et al., *Electrophoresis*, 33, 1746-1754 (2012)). Elution of bound glycomolecules from lectins may be achieved by low pH, for example glycine-HCl buffer (at pH 2-2.8) or 100 mM acetic acid; yet low pH exposure can potentially alter glycan structure. Alternatively, glycomolecule elution from lectins can be accomplished using the appropriate sugar to displace the bound glycomolecule from the immobilized lectin but the added sugar will complicate most downstream analyses.

Typically mass spectrometry analysis of a sample having a mixture of peptides and glycopeptides (both O-linked and N-linked) reveals a highly complex pattern of peaks. The primary problem is that this complex pattern cannot be interpreted to identify and characterize the individual glycomolecules in the sample. Therefore, a need exists for an enrichment reagent that is able to selectively isolate an individual class of glycomolecule, for example either N-glycan linked glycomolecules or O-glycan linked glycomolecules. Upon fractionation of a complex sample, the results of the mass spectrometry analysis might be more easily interpreted.

Many important biological activities are affected by protein glycosylation, including protein folding, protein metabolism, protein-protein interactions, immune cell recognition and intercellular signaling. Given the emerging interest in glycoproteins as biomarkers, a need exists for readily analyzing and characterizing protein glycosylation.

SUMMARY

In general, a fusion protein is provided having an amino acid sequence with at least 90% identity to SEQ ID NO: 1 and linked to an immobilization module. A protein having an amino sequence with at least 90% sequence identity with SEQ ID NO: 1 is exemplified by a protein having at least at least 90% identical to SEQ ID NO: 2.

In a further example of the fusion protein described above, the immobilization module may be a variant of $O^6$-alkylguanine-DNA alkyltransferase (AGT). Also see SEQ ID NOs: 3 and 4.

In general a protein is provided that is a sequence variant of SEQ ID NO: 2, having one or more mutations, wherein a mutation is positioned at one or more positions selected from position 154, 155, 156, 173, and 174 for example wherein the mutation at position 154 is a P, at position 155 is an A, G or P at position 156 is an S or an R, at 173 is a Y or at position 174 is an R. In one aspect, the protein is fused to an immobilization module. In one aspect, the immobilization module is a variant of AGT.

In general, a method is provided that includes the steps of a) combining a binding reagent capable of selectively binding charged and/or uncharged N-glycans or N-glycan linked glycomolecules and not binding any O-glycans; b) binding with substantially no bias, the charged or uncharged N-glycan glycomolecule to the binding reagent in a first buffer; and c) releasing the N-glycan glycomolecules from the binding reagent with a second buffer which does not comprise SDS or an oligosaccharide. The first and second buffers can be volatile for mass spec. High salt conditions may be preferred depending on the binding reagent. The methods and reagents need not chemically alter the N-glycans before capture. The captured N-glycans and/or N-glycan linked glycomolecules can be readily analyzed for glycan structure and/or glycan attachment site information.

In one aspect a method is provided that includes: a) combining a complex mixture comprising N-glycans and/or N-glycan linked glycomolecules with a binding reagent that selectively binds a core pentasaccharide, Man(α1-3)(Man(α1-6))Man(β1-4)GlcNAc(β1-4)GlcNAc (abbreviated as Man3GlcNAc2 or M3N2), in N-glycans; b) capturing the core pentasaccharide in N-glycans and/or N-glycan linked glycomolecules by the binding reagent in a first buffer for substantially unbiased binding of charged and uncharged N-glycans in the glycomolecules; and c) releasing the bound N-glycans and/or N-glycan linked glycomolecules from the binding reagent with a second buffer which does not comprise SDS or an oligosaccharide.

In one aspect of the method, the binding reagent comprises an amino acid sequence with at least 90% identical to SEQ ID NO: 1. In another aspect of the method, the binding reagent comprises an amino acid sequence with at least 90% sequence identity to SEQ ID NO: 2. In another aspect, the binding reagent comprises an amino acid sequence with at least 90% sequence identity to SEQ ID NO: 2 and a mutation positioned at one or more positions selected from position 154, 155, 156, 173, and 174. In another aspect, the binding reagent further comprises an immobilization module.

In another aspect, the immobilization module is an AGT. In another aspect, the binding reagent is immobilized.

In some embodiments, the binding reagent is free in solution. In some embodiments, the binding reagent bound with N-glycans or N-glycan linked glycopeptides is separated from other glycans or non-N-glycan linked glycopeptides or peptides or other small molecules using a filter or membrane having a discriminating pore size. In other aspects the binding reagent is immobilized on a matrix.

In one aspect, the glycomolecule is a product of enzyme cleavage, wherein the enzyme is selected from the group consisting of a glycosidase, a sialidase, a DNase, an RNase, or a combination thereof. In one aspect, the cleavage enzyme is selected from the group consisting of is trypsin, endoproteinase GluC, endo proteinase AspN, proteinase K, Factor Xa protease, IdeS, IdeE, enterokinase, furin, endonuclease S, neuraminidase, peptide-N-glycosidase Ar (PNGase Ar), peptide-N-glycosidase A (PNGase A), peptide-N-glycosidase F (PNGase F), O-glycosidase, endoglycosidase D (endo D), endoglycosidase F (endo F), endoglycosidase F1 (endo F1), endoglycosidase F2 (endo F2), endoglycosidase F3 (endo F3), endoglycosidase H (endo H), endoglycosidase S (endo S), beta1-3 galactosidase, beta1-4 galactosidase, alpha1-3,6 galactosidase, beta-N-acetylglucosaminidase, alpha-N-acetylgalactosaminidase, beta-N-acetylhexosaminidase, alpha1-2,3 mannosidase, alpha1-6 mannosidase, neuraminidase, alpha2-3 neuraminidase, alpha1-2 fucosidase, DNase, RNase H, or a combination thereof. In another aspect, the glycomolecule is a polypeptide which may be a product of protease digestion.

In one aspect of the compositions and/or methods, the N-glycan linked glycomolecule is an N-glycan, an N-glycan linked glycopeptide, an N-glycan linked glycoprotein, or a combination thereof. In some embodiments, the N-glycan moiety is labeled, unlabeled, or a mixture thereof. In some embodiments, the N-glycan linked glycomolecule is native or denatured.

In some embodiments, the N-glycan and/or N-glycan linked glycomolecules may be in or from a sample of an in vitro cell culture, a bodily fluid, a bodily secretion, a cell, a tissue, an environmental sample, or a combination thereof. Such samples can be from a human, animal, plant, bacteria, soil sample, In one aspect, the second buffer for eluting immobilized N-glycans and/or N-glycan linked glycomolecules includes one or more reagents selected from acetonitrile, water, dichloromethane, dichloroethane, pentahydrofuran, ethanol, propanol, isopropanol, methanol, nitromethane, toluene, DMSO, acetic acid, formic acid or a mixture thereof. In some embodiments, the second buffer comprises acetic acid, formic acid or other acidic solutions. In some embodiments, the second buffer is volatile. In one aspect, the second buffer includes acetonitrile.

In some embodiments, the buffer for unbiased binding of charged and uncharged N-glycans comprises a high salt concentration. For example, in some embodiments, the high salt concentration is at least 500 mM, 750 mM, 1 M, 1.5 M, 2 M, 2.5 M, or 3 M. In some embodiments, the salt is selected from ammonium acetate, ammonium chloride, ammonium sulfate, calcium acetate, calcium chloride, magnesium acetate, magnesium chloride, magnesium sulfate, potassium acetate, potassium chloride, potassium sulfate, sodium acetate, sodium chloride, and sodium sulfate or a mixture thereof. Volatile reagents in the first and second buffers are preferred for mass spectrometry.

In one aspect, the method includes analyzing the composition of the N-glycan and/or N-glycan linked glycomolecules using an analytical test selected from mass spectrometry, chromatography, electrophoresis, nuclear magnetic resonance spectrometry and fluorescence-mediated detection, or a combination thereof.

In another aspect, the method includes characterizing at least one of: the structure of the N-glycans, the linkage site of the N-glycan on the N-glycan linked glycomolecule, and/or an amount of one or more different N-glycans, or a combination thereof.

In general a method is provided for treating a patient with a hearing loss, neurofibrillary tangles and/or virus infection; comprising administering an effective dose of a truncated ubiquitin ligase that has enhanced binding to N-glycans on glycomolecules.

In one aspect, the truncated ubiquitin ligase has a sequence of at least 90% sequence identity with SEQ ID NO: 2. In another aspect, the truncated ubiquitin ligase has one or more mutations at positions corresponding to any of 154, 155, 156, 173, or 174 of SEQ ID NO: 2.

BRIEF DESCRIPTION OF THE DRAWINGS

The figures and drawings are intended to illustrate one or more versions of the compositions and/or methods described herein. Unless stated otherwise, these are not intended to be limiting for the purpose of interpreting the scope of any claims.

FIG. 2A is an SDS-PAGE gel showing that RNaseB is bound by bead-immobilized SNAP-Fbs only when the N-linked glycan is present.

Lane 1 is a control (CTL) showing the amount of input RNaseB.

Lane 2 is the result of incubating Fbs beads with RNaseB pre-treated with PNGaseF to remove N-linked glycans.

Lane 3 is the result of incubating Fbs beads with untreated RNaseB. RNaseB was eluted by boiling in SDS-containing gel loading buffer (lanes 2 and 3).

Figure 2A:
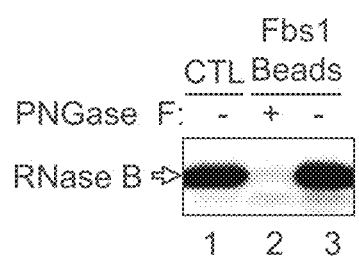
FIGS. 2A and 2B demonstrate that Fbs binding to glycomolecules is glycan-dependent.
Figure 2B:
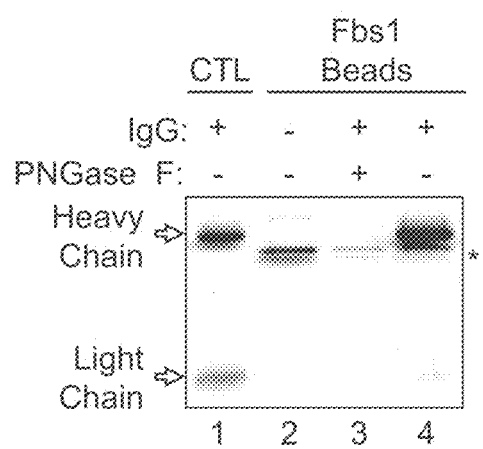

FIG. 2B is an SDS-PAGE gel showing that human IgG is bound by bead-immobilized Fbs only when N-linked glycan is present. Human IgG typically contains a glycan modification at amino acid position Asn297 of the heavy chain. Thus, Lanes 3 and 4 show that only the heavy chain is bound by Fbs beads and only when glycan is present (Lane 4).

Lane 1 is a loading control showing the mobility of light chain versus heavy chain.

Lanes 2, 3 and 4, show a small amount of SNAP-Fbs protein that is released from the beads during boiling in SDS-containing gel loading buffer to elute bound heavy chain (see asterisk).

Figure 3:
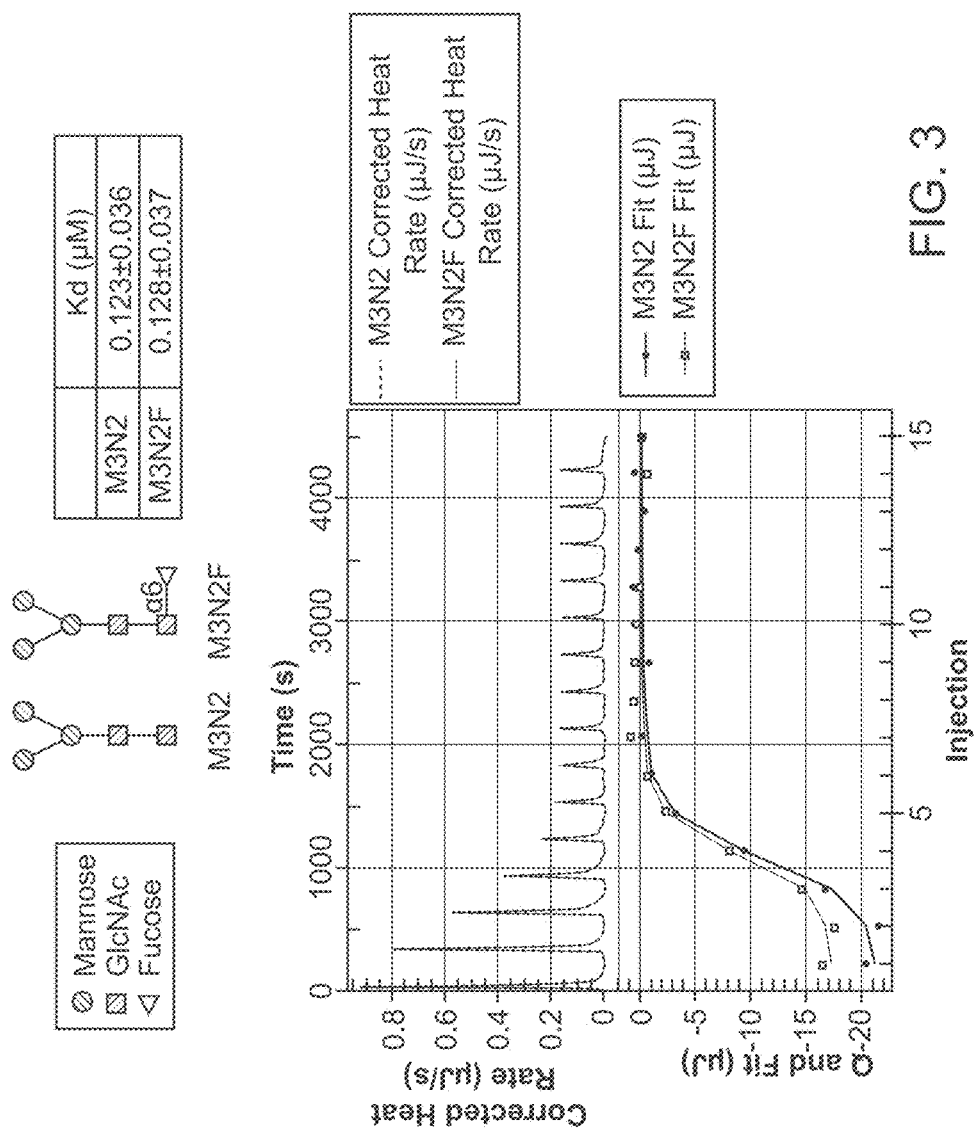

FIG. 3 demonstrates that (alpha 1-6) fucosylation of the core pentasaccharide (M3N2) structure does not affect binding of SNAP-Fbs to N-glycans (see Example 5). Two cartoons show the position of (alpha 1-6) fucosylation that is found at the reducing end of GlcNAc in some native N-glycan linked glycomolecules. The isothermal titration calorimetry data demonstrates that the affinity between the binding reagent and both M3N2 and fucosylated M3N2 (M3N2F) is nearly the same. The affinity of the binding reagent for Man3GlcNAc2 (Kd M3N2=0.123±0.036 µM) is very similar to the affinity of the binding reagent for Man3GlcNAc2 modified with fucose (Kd M3N2F=0.128±0.037 µM) indicating that N-glycan binds to the binding reagent tightly and fucosylation of the first GlcNAc residue from the reducing end does not impair binding by the binding reagent.

Figure 4:
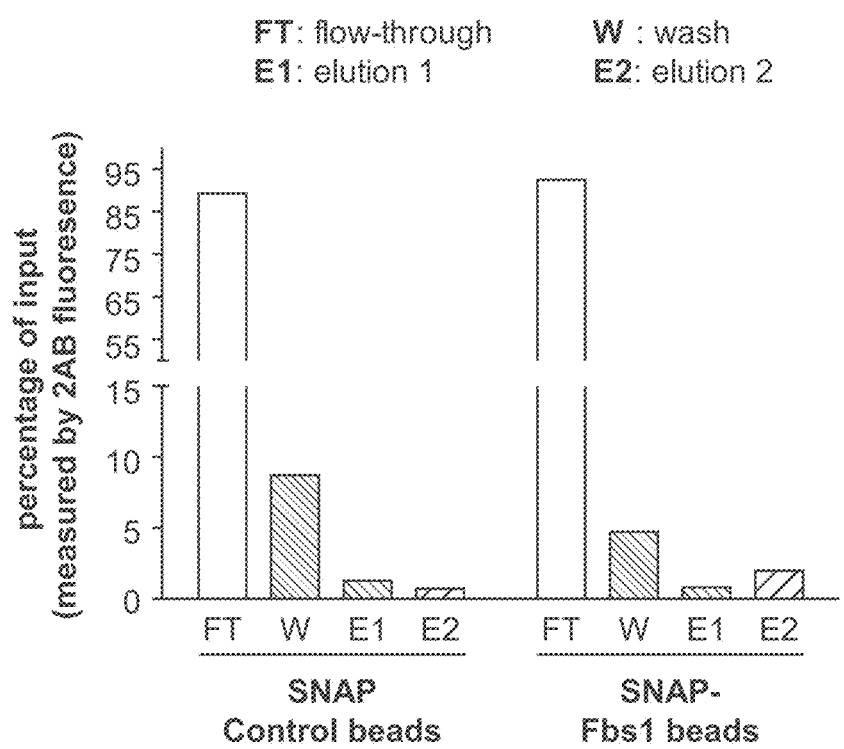

FIG. 4 shows that 2-aminobenzamide (2-AB) fluorophore labeling at the reducing end of the M3N2 completely abolishes binding by SNAP-Fbs beads. The binding and elution profiles of 2-AB labeled M3N2 that was incubated with SNAP-Fbs beads were compared with SNAP only control beads.

Figure 5:
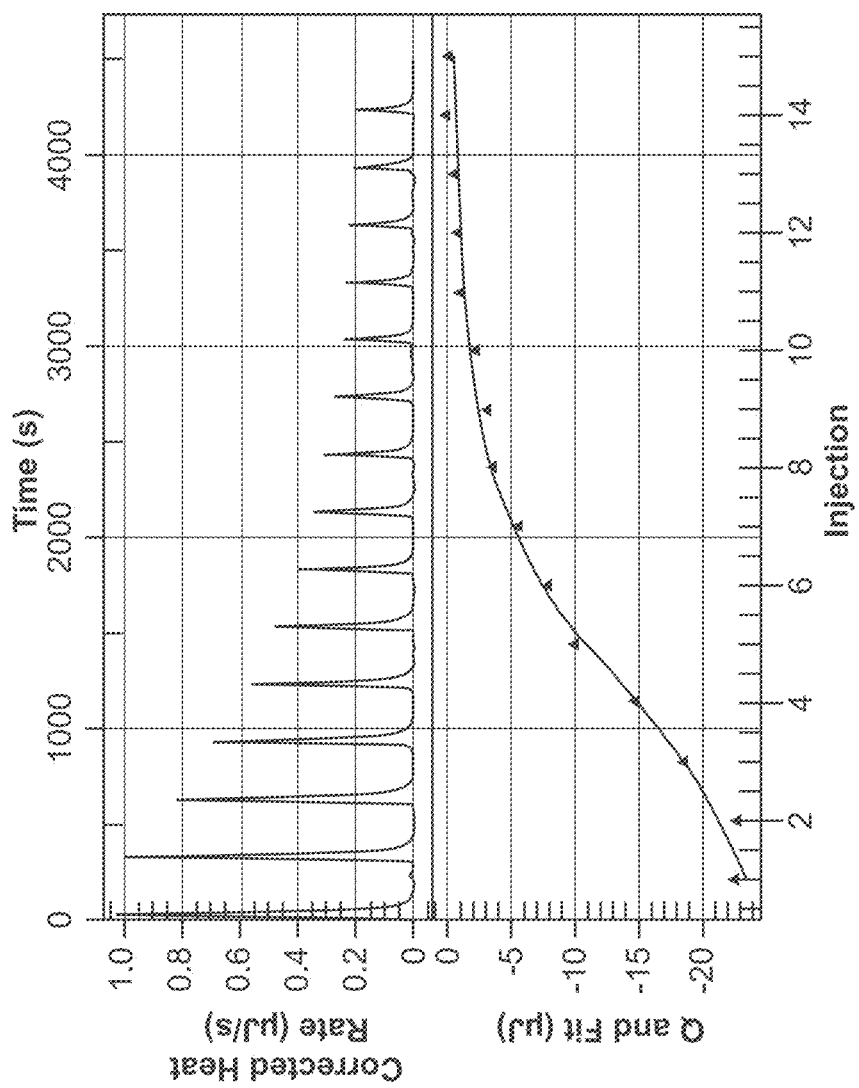
Figure 5:
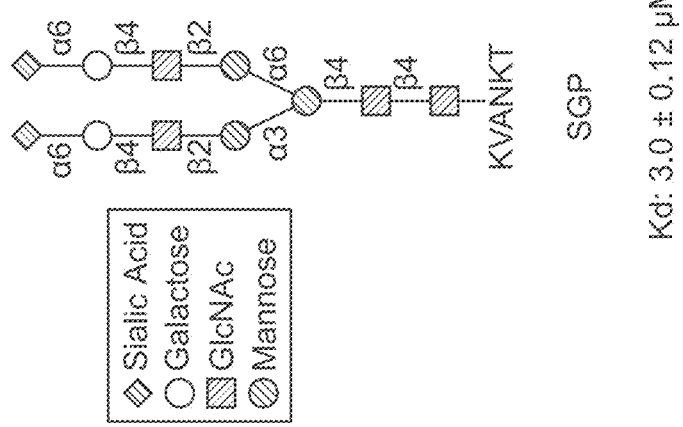

FIG. 5 demonstrates that wild type Fbs (wtFbs) binds to complex-type N-glycans containing sialic acids (see Example 6). The test glycomolecule is sialylglycopeptide (SGP, structure shown). Isothermal titration calorimetry determines that SNAP-wtFbs (in solution) can bind to SGP, calculated Kd was 3.0+/−0.12 µM.

FIGS. 6A-6C show the properties of wtFbs binding to SGP or SGP-TMR in low salt and high salt binding buffer.

FIG. 6A shows the unexpected finding that binding affinity of wtFbs to SGP-TMR is improved by a higher salt concentration (2M NaCl). High salt conditions are typically used for elution conditions, not binding conditions. However, binding of wtFbs to Asialo-SGP-TMR (lacking sialic acid) is equally efficient in low salt (50 mM NaCl) and high salt (2M NaCl).

FIG. 6B shows the effect of increasing amounts of salt (0-3000 mM ammonium acetate pH 7.5) on binding of SGP-TMR to wtFbs.

FIG. 6C shows that high salt (2M NaCl) significantly improves the binding affinity of wtFbs to sialylglycopeptide (SGP) as determined by isothermal titration calorimetry. The effect of high salt binding is a greater than 2-fold change in Kd (3.0+/−0.12 divided by 1.43+/−0.04).

Figure 7A:
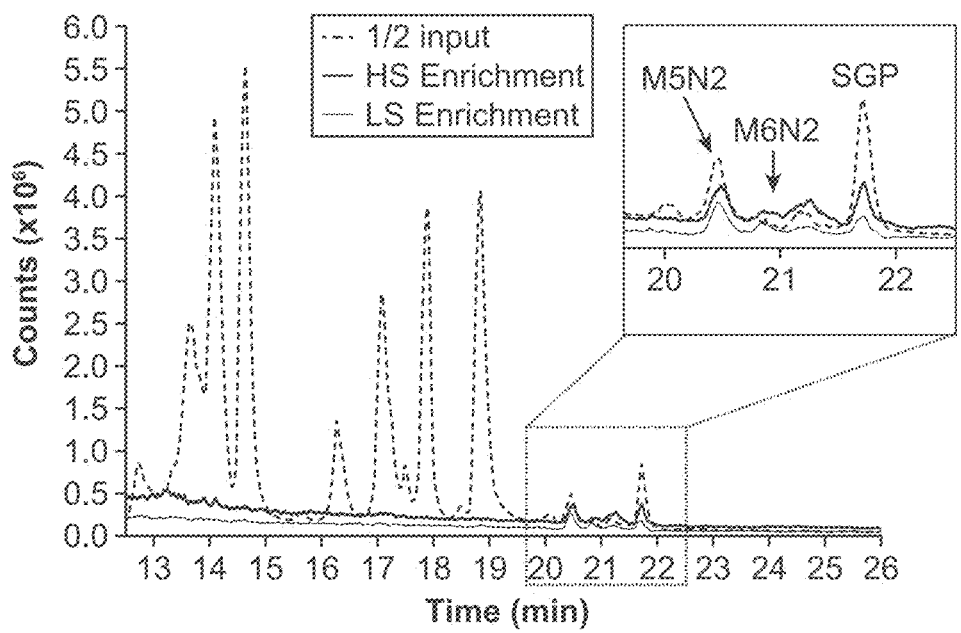
Figure 7B:
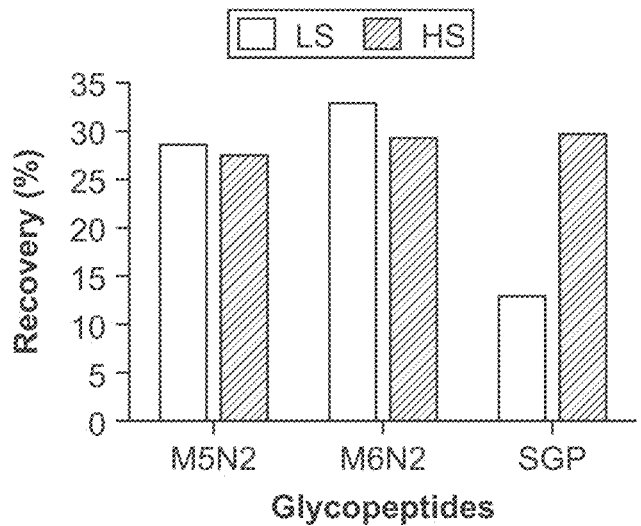
Figure 7C:
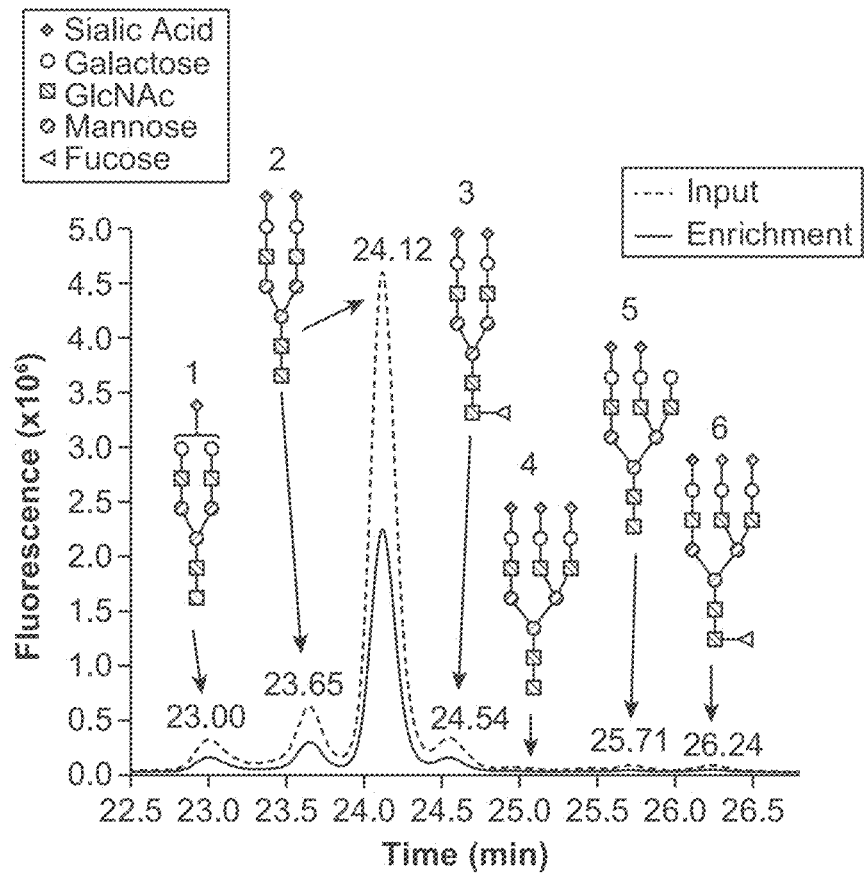

FIGS. 7A-7C show that Fbs may be employed for enrichment of N-glycan linked glycomolecules and subsequent identification and relative quantification by LC-MS (liquid chromatography coupled to mass spectrometry).

FIG. 7A is a total ion chromatogram (TIC) and enlargement demonstrating wtFbs-mediated binding and enrichment of N-glycan linked glycopeptides from a complex mixture (see Example 10). The complex mixture was a tryptic digest of RNaseB spiked with SGP to serve as a complex, sialylated glycopeptide. RNaseB contains several non-glycosylated peptides and several different high mannose N-glycan linked glycopeptides (labeled in the enlargement as: M5N2, M6N2). The dotted line indicates the chromatogram of the input mixture without enrichment. The solid black line indicates the chromatogram of the high salt (HS=2M ammonium acetate pH 7.5) enrichment sample. The solid gray line indicates the chromatogram of the low salt (LS=50 mM ammonium acetate pH 7.5) enrichment sample. The enlarged box focuses on the glycomolecules that elute between 20-22 minutes whereas the non-glycosylated peptides elute before 20 minutes. Strikingly, the non-glycosylated peptides were not enriched. N-glycan linked glycopeptides present in the sample were selectively bound by the binding reagent.

FIG. 7B is an extracted ion chromatogram which provides a quantification of the mass spectrometry data from FIG. 7A. wtFbs binding reagent significantly enriched for N-glycan linked glycopeptides and the enriched sample is substantially unbiased when using high salt binding conditions.

FIG. 7C shows that wtFbs is able to enrich N-glycan linked glycomolecules from a tryptic digest of transferrin. When using high salt conditions (2 M ammonium acetate pH 7.5), the recovery of various types of complex glycomolecules ranged from 28.2% to 42.7%.

Figure 8:
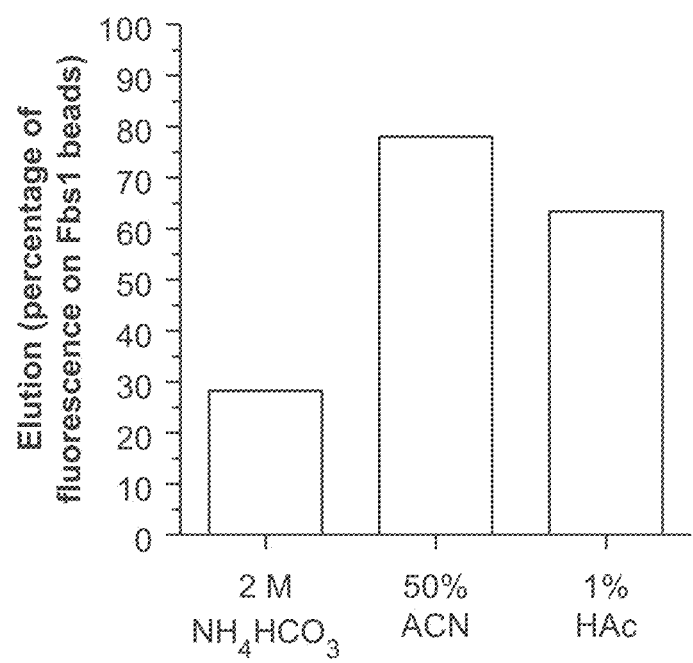

FIG. 8 compares elution buffers (see Example 10). An organic solvent (50% acetonitrile in this example) and mildly acidic conditions (1% acetic acid in this example) were significantly more efficient at eluting bound N-glycans from the binding reagent than high salt conditions (2 M ammonium bicarbonate), which was the least efficient. The test N-glycan linked glycopeptide was SGP-TMR. The y-axis is the percent of eluted labeled SGP. About 78% of SGP-TMR was eluted in the first 100 µl of 50% acetonitrile (ACN=acetonitrile; HAc=acetic acid).

Figure 9C:
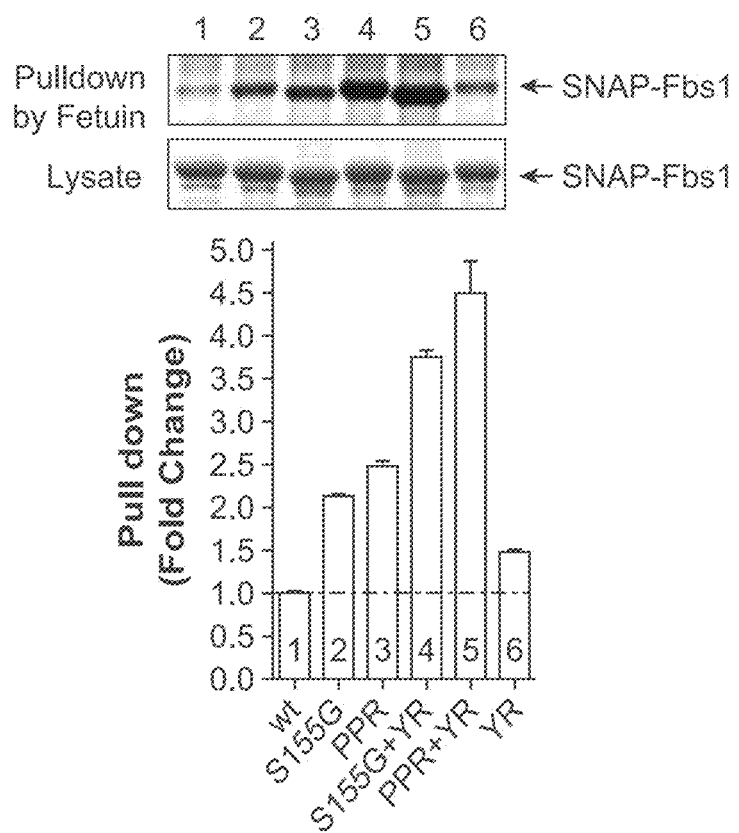

FIGS. 9A-9C serve to describe various Fbs mutants with improved binding affinity for N-glycan linked glycomolecules.

FIG. 9A shows the amino acid sequence of Fbs sugar binding domain (SBD). The SBD (position 113 to 296 in human Fbs) was expressed as a fusion to either p50 DNA binding protein or to the SNAP-tag. Bold letters indicate the positions that were subject to mutagenesis. The table shows the mutants of human Fbs that were analyzed. The top 2 rows of the table show the amino acid residues within mouse Fbs that correlate to human Fbs.

FIG. 9B demonstrates that several Fbs mutants possess increased affinity to fetuin, a complex-type N-glycan linked glycoprotein. Fetuin was conjugated to Affigel-15 beads and then incubated with wtFbs or individual Fbs mutant proteins. The top panel shows the amount of bound and eluted Fbs protein by -PAGE analysis. Image J software was used to quantify the amount of bound Fbs protein in order to generate the bar graph. Binding was carried out in low salt buffer (50 mM ammonium acetate pH 7.5).

FIG. 9C demonstrates the binding properties of combinatorial mutants of Fbs. The panel labeled "Pulldown by Fetuin" shows the amount of wtFbs or variant Fbs that binds to Affigel-Fetuin beads. The PPR mutant was combined with the YR mutant to generate quintuple mutant PPRYR, which shows the highest affinity to fetuin in low salt buffer (50 mM ammonium acetate pH 7.5). The Lysate panel shows that equivalent amounts of each Fbs protein were present in the respective cell lysates incubated with Affigel-Fetuin beads.

FIGS. 10A-10C show the binding characteristics of 2 selected Fbs mutants in comparison to wtFbs.

FIG. 10A shows that the GYR mutant and PPRYR mutant both possess increased affinity to fetuin and no change in affinity to RNaseB in low salt buffer (50 mM ammonium acetate pH 7.5). In high salt conditions (2000 mM ammonium acetate pH 7.5), the GYR mutant shows the highest affinity to both fetuin and RNaseB, which were added simultaneously to Fbs beads.

FIG. 10B shows that an equivalent amount of each SNAP-tagged test protein was conjugated to benzylguanine (BG) beads. FT indicates the amount of test protein in the flow-through after conjugation.

FIG. 10C is a table which summarizes the relative affinities of wtFbs, the GYR mutant and the PPRYR mutant to fetuin and RNaseB. A ratio of 1 or near to 1 indicates that binding affinity to fetuin (a complex-type N-glycan linked glycomolecule) and to RNaseB is unbiased. The values in the table were calculated according to ImageJ quantification of the band intensities in FIG. 10A.

Figure 11:
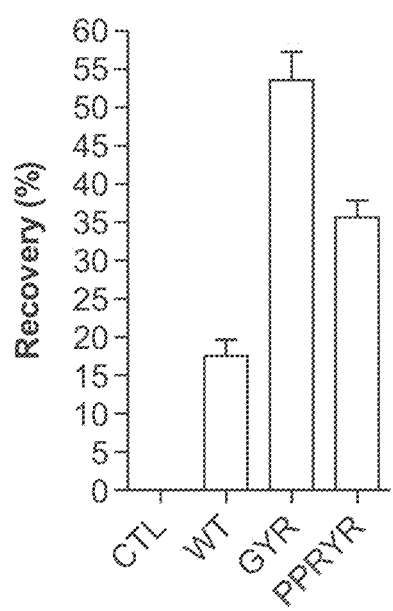

FIG. 11 shows the relative binding affinities of wtFbs, the GYR mutant and the PPRYR mutant to SGP-TMR. Each Fbs protein was conjugated to BG beads and then incubated with SGP-TMR. After incubation at 4° C. for 1 hour, the Fbs beads were centrifuged and the unbound SGP-TMR in the supernatant was measured. Recovery (%) is the amount of bound glycomolecule and was calculated by measuring fluorescence of the input solution and then subtracting the amount of fluorescence in the supernatant. The GYR mutant possesses superior binding affinity to this sialylated substrate in low salt buffer (50 mM ammonium acetate pH 7.5).

DETAILED DESCRIPTION

Described herein are methods and compositions described for specifically capturing N-glycan and/or N-glycan linked glycomolecules in a substantially unbiased manner without the need for irreversible changes to the N-glycan composition or structure and without the need for multiple binding reagents. Advantageously, the captured N-glycan linked glycomolecules can be released under conditions that are compatible with standard downstream analytical protocols.

Unless defined otherwise, all technical and scientific terms used herein have the same meaning as commonly understood by one of ordinary skill in the pertinent art. Embodiments described herein may include one or more ranges of values (e.g., size, concentration, time, temperature). A range of values will be understood to include all values within the range, including subset(s) of values in the recited range, to a tenth of the unit of the lower limit unless the context clearly dictates otherwise.

As used herein, the articles "a", "an", and "the" relate equivalently to a meaning as singular or plural unless the context dictates otherwise.

A "glycomolecule" here refers to a non-carbohydrate entity such as lipids, proteins or other biological or non-biological molecules to which is attached one or more carbohydrate moieties.

Examples of glycomolecules are glycoproteins which include proteins, polypeptides or peptides to which is linked one or more glycans. The protein or a proteolytically cleaved glycoprotein may have a size suitable for mass spectrometry analysis. For example, a proteolytically cleaved glycoprotein may have an amino acid composition of less than 500 amino acids for example, less than 400 amino acids, for example, less than 300 amino acids, for example, less than 200 amino acids. In one embodiment, the proteolytically cleaved glycoprotein has less than 150 amino acids.

Glycosylation refers to the covalent attachment of a glycan to a polypeptide, lipid, polynucleotide or another glycan. The terms "glycosylated peptide" "glycosylated polypeptide" or "glycosylated protein" can be used interchangeably with "glycopeptide," "glycopolypeptide" or "glycoprotein."

Wherever N-glycan linked glycomolecules react with the binding reagent, it is expected that the binding reagent will react in a similar manner with N-glycans that have been cleaved from the N-glycan linked glycomolecules.

A "glycan" refers to a carbohydrate entity that has (a) a pentasaccharide core structure with a GlcNAc at its reducing end capable of covalent linkage to the amine group on the side chain of asparagine in a protein, polypeptide or peptide (N-glycan); (b) an oligosaccharide with a GalNAc capable of forming a covalent bond with a hydroxyl group on the side chain of a serine or threonine (O-glycan); or (c) other carbohydrate entities capable of covalent linkage to a protein or lipid.

An N-glycan may have a fucose at the reducing end, linked to the GlcNAc. In one embodiment, N-glycans may have one or more sialic acids at the non-reducing ends of the pentasaccharide core. In another embodiment, the pentasaccharide core may have alternative branches of saccharides or additional saccharides extensions on the core branches. One or more sialic acids may be found on these alternative branches or extensions of the glycan.

The sialic acids including variants thereof impart charge to the glycans hence the term "charged".

The attachment of glycans to proteins, polypeptides or peptides is referred to herein as glycan-linked glycomolecules. Those glycomolecules that are enriched by embodiments described herein contain N-linked glycans but may also contain O-linked glycans and/or other carbohydrate entities. These are "N-glycan linked glycomolecules".

The terms "enriched" or "enriching" refers to a reduction in complexity of a mixture. Here the representation of N-glycan linked glycomolecules may be increased by more than 50%, 60%, 70%, 80%, 90%, 100%, 150%, 200%, or more compared to an un-enriched solution.

The terms "substantially unbiased" refer the capacity of the binding reagent to bind to an N-glycan either alone or linked to a protein, peptide or polypeptide regardless of its composition or linkage position. The term "substantially" refers to at least 50%, 60%, 70%, 80%, 85%, or 90%. One example shows substantially unbiased binding resulting in 65% recovery and a second example shows about 90% recovery of a charged N-glycan linked glycoprotein based on a comparison with recovery of an uncharged N-glycan linked glycoprotein.

The term "cleavage enzyme" refers to enzymes for cleaving proteins, polypeptides or peptides such as proteases; enzymes that cleave glycans from glycomolecules such as amidases such as PNGase; enzymes that cleave between adjacent sugar residues such as exoglycosidases or endoglycosidases and enzymes that cleave contaminating nucleic acids from cell lysates such as DNAases and RNases. Further examples of cleavage enzymes include trypsin, endoproteinase GluC, endo proteinase AspN, proteinase K, Factor Xa protease, IdeS, IdeE, enterokinase, furin, endonuclease S, neuraminidase, PNGase Ar, PNGase A, PNGase F, O-glycosidase, endo D, endo F, endo F1, endo F2, endo F3, endo H, endo S, beta1-3 galactosidase, beta1-4 galactosidase, alpha1-3,6 galactosidase, beta-N-acetylglucosaminidase, alpha-N-acetylgalactosamindiase, beta-N-acetylhexosaminidase, alpha1-2,3 mannosidase, alpha1-6 mannosidase, neuraminidase, alpha2-3 neuraminidase, alpha1-2 fucosidase, DNase, RNase H, or a combination thereof.

An "immobilization module" refers to a protein, nucleic acid, synthetic molecule or other chemicals capable of coupling with a binding reagent for purposes of immobilizing the N-glycan linked glycoproteins by affinity binding. Examples of immobilization modules are known in the art and include: maltose-binding proteins (MBPs) (U.S. Pat. Nos. 5,643,758 and 7,825,218; 7,883,867, and 8,623,615), SNAP-TAG® (New England Biolabs, Ipswich, Mass.) (utilizing AGT, see U.S. Pat. Nos. 7,939,284, 8,367,361, 7,799,524, 7,888,090, 8,163,479, and 8,178,314), CLIP-TAG™ (utilizing ACT, see U.S. Pat. Nos. 8,227,602 and 8,623,627), inteins (U.S. Pat. Nos. 5,496,714, 5,834,247, 6,521,425, 7,157,224, 6,849,428, 7,001,745, 6,858,775, and 7,271, 256), chitin-binding proteins (U.S. Pat. Nos. 6,897,285, 7,060,465, 6,984,505, and 6,987,007), biotin, streptavidin, antibodies, or Flag-tags.

"Labeling" of N-glycans or N-glycan linked glycomolecules includes labeling the N-glycans and/or labeling the non-carbohydrate entity. Labeling of glycans can be achieved using any label known in the art including: 2-AB, (Anthranilamide, Anthranilic acid amide), Anthranilic acid (2AA) (2-Aminobenzoic acid), 2-Aminopyridine (2-AP) (2-Pyridinamine, 2-Pyridylamine), 2-aminonaphthalene trisulfonic acid (ANTS), 1-aminopyrene-3,6,8-trisulfonic acid (APTS), 1-phenyl-3-methyl-5-pyrazolone (PMP), 2,6-Diaminopyridine (DAP), 4-Aminobenzamidine (4AB), 7-Amino-4-methylcoumarin (AMC), procainamide, RapiFluor-MS™ (Waters, Milford, Mass.), aminoxyTMT™ (Life Technologies, Carlsbad, Calif.), and IMS (Prozyme, Hayward, Calif.) (also see Ruhaak, et al., *Anal Bioanal Chem.* 397, 8, 3457-3481 (2010); Kalay, et al., *Anal Biochem.*, 423, 1, 153-62 (2012); and Radoslaw, et al., *Analytical* Biochemistry, Available online 12 Jun. 2015). Labeling of non-carbohydrate entities may occur for fusion molecules through labeling an immobilization module (for example, modified benzyl guanine substrate for AGT) or by direct labeling of the non-carbohydrate entity or by utilizing a nucleic acid aptamer labeled with a tag and capable of associating with the non-carbohydrate entity.

A "binding reagent" is described in more detail below and refers to a reagent that specifically and selectively binds N-glycan linked glycomolecules. In one embodiment, the binding reagent includes a SBD of a polypeptide such as for example, the SBD of F-box sugar domain (Fbs). In one aspect, the binding reagent comprises a consensus sequence of a polypeptide that has 70%, 75%, 80%, 85%, 90%, 95%, 99% or 100% sequence identity to SEQ ID NO: 1.

(SEQ ID NO: 1)
$F_{113}$YFLSKRRRNLXXNXCGXXXLXXWXXVEXGGDGWXXEXLPGDXGXXF

XXXXXVXKXFXXSXEWCRKXQXXDLXAEGYWEELLDXXQPXXXXKDWYXG

RXDAGXXYELXVKLLSXXEXVLAEXXXXXXAXPXXXXXXXWXXISXTFXX

YGPGVRXXRFXHXGQDXXXWKGWXGXRXTNSSVXVXP, wherein X is any amino acid.

X may be selected from the following amino acids in Table 1:

TABLE 1

| | | | |
|---|---|---|---|
| $X_{12}$, may be L or I | $X_{56}$ may be Y or F | $X_{114}$ may be V or E | $X_{146}$ may be T or S |
| $X_{18}$, may be E or D | $X_{58}$ may be A or V | $X_{115}$ may be H or N | $X_{154}$ may be F or Y |
| $X_{19}$, may be E or D | $X_{59}$ may be S or T | $X_{117}$ may be D or N | $X_{155}$ may be V or I |
| $X_{20}$, may be E or D | $X_{61}$ may be F or Y | $X_{122}$ may be F or Y | $X_{158}$ may be E or Q |
| $X_{22}$, may be E or Q | $X_{67}$ may be A or S | $X_{124}$ may be S or T | $X_{160}$ may be A or G |
| $X_{23}$, may be G or H | $X_{69}$ may be V or I | $X_{125}$ may be G or E | $X_{165}$ may be V or L |
| $X_{26}$, may be E or D | $X_{70}$ may be V or I | $X_{126}$ may be Q or T | $X_{166}$ may be Y or F |
| $X_{29}$ may be H or N | $X_{88}$ may be A or K | $X_{127}$ may be V or I | $X_{171}$ may be Y or F |
| $X_{35}$ may be R or K | $X_{89}$ may be I or V | $X_{129}$ may be V or I | $X_{173}$ may be A or V |
| $X_{36}$ may be V or I | $X_{90}$ may be V or M | $X_{132}$ may be D or E | $X_{175}$ may be V or M |
| $X_{38}$ may be D or E | $X_{91}$ may be V or A | $X_{136}$ may be A or G | $X_{181}$ may be W or T |
| $X_{46}$ may be E or D | $X_{96}$ may be S or A | $X_{137}$ may be G or S | $X_{183}$ may be Q or E |
| $X_{50}$ may be E or D | $X_{103}$ may be C or S | $X_{140}$ may be E or Q | |
| $X_{51}$ may be E or D | $X_{104}$ may be L or V | $X_{143}$ may be H or Y | |

In some embodiments, one example of SEQ ID NO: 1 is a polypeptide comprises an amino acid sequence at least 70%, 75%, 80%, 85%, 90%, 95%, 99% or 100% sequence identity to:

(SEQ ID NO: 2)
$F_{113}$YFLSKRRRNLLRNPCGEEDLEGWCDVEHGGDGWRVEELPGDSGVEF

THDESVKKYFASSFEWCRKAQVIDLQAEGYWEELLDTTQPAIVVKDWYSG

RSDAGCLYELTVKLLSEHENVLAEFSSGQVAVPQDSDGGGWMEISHTFTD

YGPGVRFVRFEHGGQDSVYWKGWFGARVINSSVWVEP$_{296}$.

This truncated protein corresponds to the SBD of an N-glycan binding ubiquitin ligase.

Sequence identity can be determined by those of skill in the art using standard techniques, including sequence algorithms like BLAST (Altschul, et al., *J. Mol. Biol.* 215, 403-410 (1990); Altschul, et al., *Nuc. Ac. Res.* 25, 3389-3402 (1997) and FASTA, Pearson and Lipman, *PNAS* 85, 8, 2444-2448 (1988)).

Variants of SEQ ID NO: 2 have been generated to obtain greater binding affinity to N-linked glycan glycomolecules or N-glycans than the truncated non mutated Fbs protein. An added benefit is that the variants do not rely on a high salt binding buffer for optimal binding to N-glycans and N-linked glycan glycomolecules which is the preferable option for the wild type protein. Examples of advantageous mutation sites are provided in Table 2. Table 2 describes 5 different mutation positions: 154, 155, 156, 173 and 174 where the numbering corresponds to SEQ ID NO: 2. As shown in the table, mutations assigned to these positions are for D154P, S155A, S155G, S155P, G156S, G156R, F173Y and E174R. It was shown that the mutations individually or in various combinations were capable of improving binding. The combinations may include single mutations, double mutations, triple mutations, 4 mutations, or 5 mutations selected from those in table 2. The benefits of single mutations and a plurality of mutations are illustrated in FIGS. 9A-9C and FIG. 10A-10C and FIG. 11.

Binding reagents exemplified by SEQ ID NO: 1 and SEQ ID NO: 2 may be fused to an immobilization module (see for example SEQ ID NO: 4) to form a fusion protein (SEQ ID NO: 3). Other examples of immobilization modules include peptides with at least 80%, 85%, 90%, 95%, 98% or 99% sequence identity with SEQ ID NO: 4.

The improved binding of mutant Fbs to N-glycans and N-glycan linked glycomolecules suggests that the mutants may be used to reduce BACE1 levels and reduced synaptic deficits in Alzheimer patients (see Ohtsubo, et al., *Sugar Chains: Decoding the function of Glycans*, p. 9 (2015)). Another glycoprotein that is involved in Alzheimer's disease is the amyloid precursor protein (APP) whose cleavage products, particularly amyloid-β, accumulate in Alzheimer disease (AD). APP is present at synapses and is thought to play a role in both the formation and plasticity of these critical neuronal structures. Wild type Ubiquitin ligase Fbxo2 is believed to regulate APP levels and processing in the brain and may be a therapeutic approach to modulating AD pathogenesis and associated symptoms. It is proposed here that Fbs variants described herein would improve the efficacy of this beneficial effect.

Another use for Fbs variants is as an antiviral agent. Many viruses have glycomolecules on their surface such as Ebola virus, herpes virus and influenza virus and many others. Fbs variants are expected to efficiently interact with envelope glycoproteins to prevent infection of new cells.

Another use for Fbs variants is for counteracting hearing loss associated with aging and deterioration of inner ear homeostasis.

The role of glycoproteins in health and disease is extensive although not yet well understood. Fbs variants that bind to glycomolecules in membranes of cells may prove to be very useful therapeutic agents and may further increase the understanding of the role of glycoproteins for diseases where glycomolecules from host and/or pathogen are incorrectly folded in viva Fbs variants may be substituted for other variants having a consensus sequence (SEQ ID NO: 1) or binding reagents that mimic the function of these variants.

TABLE 2

Variants having increased binding affinity for N-glycans and N-glycan linked glycomolecules.

|  |  | a.a. position | 158 | 159 | 160 | 177 | 178 |
|---|---|---|---|---|---|---|---|
| Mouse FbS1 | wt |  | D | N | G | F | E |
|  |  | a.a. position | 154 | 155 | 156 | 173 | 174 |
| Human Fbs | wt |  | D | S | G | F | E |
|  | S155A |  | D | A | G | F | E |
|  | S155G |  | D | G | G | F | E |
|  | PPG |  | P | P | G | F | E |
|  | PPS |  | P | P | S | F | E |
|  | PPR |  | P | P | R | F | E |
|  | YR |  | D | S | G | Y | R |
|  | S155G + YR |  | D | G | G | Y | R |
|  | PPR + YR |  | P | P | R | Y | R |

In some embodiments, the binding reagent is a fusion protein. For example, any of the above polypeptide can be fused to one or more reagents that can serve as a label, tag, or immobilization module. Examples of labels include fluorescent, chemiluminescent, or radioactive labels.

The fusion protein may be immobilized on a two dimensional matrix such as filter paper or a three dimensional matrix such as a polymer that forms a fabric or a polymer or a surface of a device such as a microfluidic device.

Figure 1:
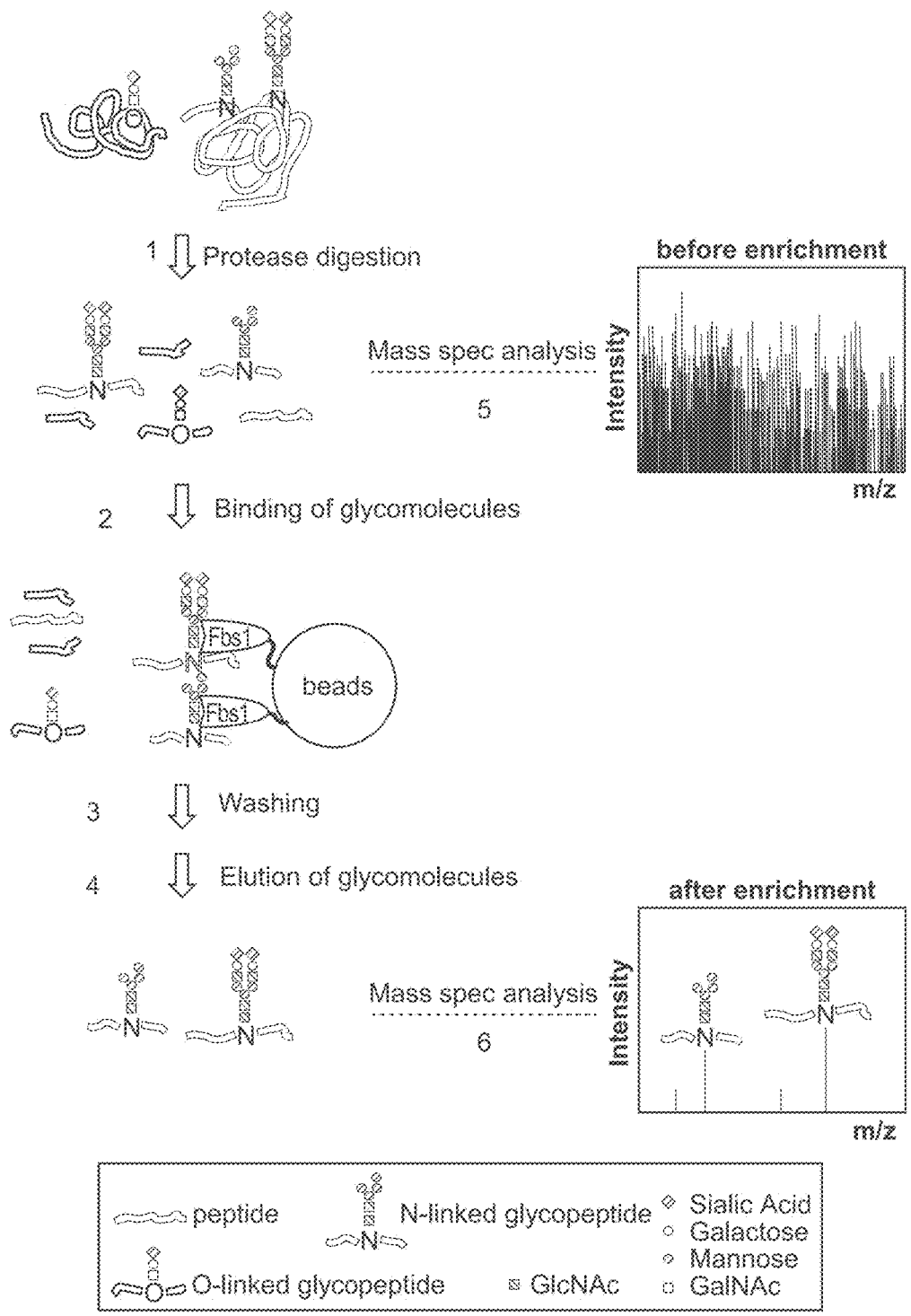
FIG. 1 outlines one example embodiment of the methods described herein. Mass spectrometry analysis of a sample having a mixture of peptides, glycopeptides (both O-glycan linked and N-glycan linked) reveals a highly complex pattern of peaks (see box labeled "before enrichment"). Complex patterns cannot be interpreted to identify and characterize the individual glycomolecules in the sample. Here, a clear mass spectroscopic analysis is provided in (Step 6) that can identify and characterize all N-glycan linked glycomolecules present in the sample (see box labeled "after enrichment"). Step 1 is protease digestion of a glycoprotein to generate fragments where some of the fragments have glycans while others do not. Mass spectrometry at this stage (Step 5) reveals a complex result. However, if the analysis proceeds to (Step 2) which includes the binding of the glycan peptide fragments to Fbs coated beads in a suitable buffer and (Step 3) which involves washing and then elution of the glycopeptides, then mass spectrometry reveals a simplified pattern which can be readily and accurately analyzed.

FIG. 1 shows the work flow that results in an enriched N-glycan linked peptide that can be analyzed by mass spectrometry or by other analytical techniques such as chromatography, electrophoresis, nuclear magnetic resonance spectrometry and fluorescence-mediated detection, or a combination thereof.

A glycomolecule sample can be derived from any source such as for example, a biological fluid such as blood, serum, urine or mucose, a fermentation media containing secreted cell products, cell lysate from a biopsy or fermentation may be analyzed by a workflow as demonstrated in FIG. 1. N-glycan linked glycomolecules can be in or from a sample of a recombinantly synthesized, chemically synthesized, an environmental sample (e.g., soil, water, air, surface swab). Such sources include animals (including humans, domesticated and non-domesticated animals), avian, insect, aquatic, bacteria, viruses and plants.

In some embodiments, the N-glycan linked glycomolecule sample is a complex mixture. For example, the complex mixture may contain multiple N-linked glycan glycomolecules as well as other non-N-glycan linked glycomolecules. For example, when the sample is a body fluid such as serum or plasma, the sample contains not only many different N-linked glycan glycomolecules, but also non-carbohydrate entities that do not have N-glycans such as lipids, DNA, RNA, organelles, whole cells and fragments of cells.

In some embodiments, the N-linked glycan glycomolecules can be native or denatured. For example, the N-linked glycan glycomolecules can be denatured by heat treatment, exposure to a reducing agent or other agents that tend to disrupt the native conformation.

Embodiments of the binding reagents provided herein selectively and reversibly binds to all N-linked glycan glycomolecules, because the binding reagents target a core pentasaccharide N-glycan structure at the reducing end of the glycan irrespective of whether the N-glycan is charged or uncharged. Charged N-glycans may contain a sialic acid linked to the terminal mannose on the forked structure shown in FIGS. 1, 5, 7C. Examples of N-glycans, include high mannose, hybrid, and complex-type N-glycans. More specifically, the pentasaccharide is Man($\alpha$1-3)(Man($\alpha$1-6)) Man($\beta$1-4)GlcNAc($\beta$1-4)GlcNAc. In some cases, a fucose may also be found attached to the ultimate GlcNAc. Surprisingly, as described in Example 5 and shown in FIG. 3, that binding of the binding reagent to the core structure is not affected by the presence of fucose on the core structure. Embodiments of the binding reagents are capable of binding N-glycans and/or N-glycan linked glycomolecules in a substantially unbiased manner. This is an important feature as it avoids under-representing or even missing N-linked glycan glycomolecules in a mixture. The Examples illustrate effective binding of charged N-linked glycan glycomolecules (see Examples 7, 9, 10, 11) under suitable salt conditions and this binding is substantially unbiased (see Examples 8, 12, 13). Prior art methods preferentially capture either charged or uncharged N-glycans, but not both.

The binding reagents described herein do not include lectins that bind GlcNAc in any position of the glycan, including the branched antennae of complex and hybrid glycans and does not target the core structure.

For cell lysates, it may be desirable to degrade DNAs and RNAs and to utilize detergents to liberate glycomolecules. If the glycomolecule of interest is an antibody, it may be desirable to bind the sample to protein A in order to obtain an enriched antibody sample. For soluble enzymes, it may be desirable to precipitate cellular material leaving the glycomolecules in the supernatant.

This step may be followed by an enzyme cleavage step. In FIG. 1, the enzyme cleavage step is accomplished by a protease which cleaves proteins into peptides. Some of peptides will have N-linked glycans.

At this stage, an attempt to perform mass spectrometry will generate a very complex profile as illustrated in FIG. 1. However, enrichment can be achieved if the cleavage products are reacted to a binding reagent that selectively binds all N-glycan linked glycopeptides. To achieve this, it was found that a high salt binding buffer substantially eliminated bias when a SBD of a binding protein (Fbs) was utilized as a binding reagent to selectively bind N-glycans linked to the glycomolecules. It was subsequently found that synthetic variants of this binding protein did not require high salt conditions in the binding reaction.

In some embodiments, the high salt concentration in a buffer, sometimes referred to herein as a first buffer, is at least or about 500 mM, 750 mM, 1 M, 1.5 M, 2 M, 2.5 M, or 3 M. Suitable salts include ammonium acetate, ammonium chloride, ammonium sulfate, calcium acetate, calcium chloride, magnesium acetate, magnesium chloride, magnesium sulfate, potassium acetate, potassium chloride, potassium sulfate, sodium acetate, sodium chloride, sodium sulfate. The Examples describe the use of such suitable salts, including sodium chloride and ammonium acetate. Unexpectedly, high salt does not disrupt the binding between the binding reagent and N-glycan linked glycomolecules.

High salt conditions are generally accepted in the prior art for use in disrupting the binding interaction between binding partners. In contrast, high salt conditions are shown herein to not disrupt the binding and instead improve binding of the binding reagent to N-glycan linked glycomolecules. Example 6 details a titration curve showing increased binding with increasing ionic strength of the buffer. Without wishing to be bound by theory, the high salt conditions may neutralize any charged N-glycan linked glycomolecules. This facilitates substantially unbiased binding of the reagent to both charged and uncharged N-glycan linked glycomolecules.

It was also shown that the binding reagents could effectively bind N-glycan linked glycoproteins when immobilized. Immobilization shown in FIG. 1 results from forming a fusion protein between the SBD of Fbs or variants thereof and a modified DNA repair enzyme called AGT. Optionally, the fusion protein may form covalent linkages with benzyl guanine derivatives that may be present in solution or form coatings on a solid, semi-solid or porous surface such as a bead or other polymer matrix such as a well, column, plate or a microfluidic device. Example 1 illustrates the use of a binding protein that is a fusion protein between SNAP-tag and Fbs and immobilization of the binding reagent on beads.

Example 1 and FIG. 1 show how the methodology is efficient for improving mass spectrometry results for purposes of identifying the site of attachment of an N-glycan on a protein, the composition of the N-glycan and/or the properties of the peptide to which the N-glycan is attached. Once the N-glycan linked glycopeptides are bound to the binding reagent and the non-binding material washed away, the N-glycan linked glycopeptides can be efficiently eluted using a second buffer. This buffer utilizes an organic solvent, acidic pH or low ionic strength for efficient release of bound N-glycan linked glycomolecules. Example 14 demonstrates suitable examples of different reagents for releasing captured N-glycan linked glycomolecules. In some embodiments, the buffer is volatile preferably comprising 50% v/v acetonitrile in water or the buffer is 1% acetic acid. Other reagents may be used such as water, dichloromethane, dichloroethane, pentahydrofuran, ethanol, propanol, isopropanol, methanol, nitromethane, toluene, DMSO, acetic acid, formic acid or a mixture thereof. Preferably SDS is not used as it interferes with mass spectrometry.

The N-glycan linked glycomolecules can be readily analyzed. For example, the N-glycan linked glycomolecules can be analyzed by mass spectrometry, chromatography, electrophoresis, nuclear magnetic resonance spectrometry and fluorescence-mediated detection, or a combination thereof. See any one of Examples 2-4, 6, 8, 9, 11-17 for examples of such analyses. The analysis of the N-glycan linked glycomolecules can characterize the structure of one or more N-glycans, identify the N-glycosylation linkage site on an N-glycan linked glycopeptide or N-glycan linked glycoprotein, quantify the amount of one or more different N-glycans, or any combination thereof. Such analyses are useful in the identification of N-glycan linked glycomolecule biomarkers, may assist in disease diagnosis, or be used to monitor disease progression or treatment.

The workflow shown in FIG. 1 is also suited for the analysis of N-glycans that may have been cleaved from proteins using a PNGase. However, such an analysis cannot provide information directly about the linkage site of N-glycan on a peptide although it can provide information on the amount and composition of the N-glycans.

The enrichment of N-glycans by binding to an immobilized binding reagent is not limited to the use of Fbs or to the use of AGT. Advantageously, the methods and reagents described herein are substantially unbiased in capturing all N-glycan linked glycomolecules, whether an N-glycan or an N-glycan linked glycopeptide or N-glycan linked glycoprotein, and whether the N-glycans are charged or uncharged. Furthermore, the methods are readily compatible with downstream analytically methods, such as mass spectrometry, which are sensitive to interference by reagents like detergents.

The methods and compositions described herein are non-natural. For example, the binding reagent is non-natural. Where the term "wild type" is used with respect to the binding agent, it refers to an isolated domain derived from a wild type protein, namely the SBD that does not itself occur naturally. Hence the wt ubiquitin ligase SBD of SEQ ID NO: 1 and 2 are non-natural. Any variant of this polypeptide is also unnatural. The variants were identified by experimentation in vitro and are not known to occur in nature either as an isolated domain or as part of a larger protein. Where the wild type is fused to an immobilization module, this is also an unnatural construction and is not known to occur in nature. The methods described herein do not mimic and cannot be construed as natural.

SEQ ID NO: 1 has been given an amino acid number of 1 for the first amino acid in the consensus polypeptide sequence. In SEQ ID NO: 2, the first amino acid is labeled as 113 which corresponds to amino acid 1 in SEQ ID NO: 1. In fact it is a truncated version of the human fbs1 protein in which the first 112 amino acids have been removed. SEQ ID NO: 2 is one example of the consensus sequence described by SEQ ID NO: 1 and is not intended to be limiting.

(SEQ ID NO: 3)
MGSSHHHHHHGDKDCEMKRTTLDSPLGKLELSGCEQGLHEIKLLGKGTSA

ADAVEVPAPAAVLGGPEPLMQATAWLNAYFHQPEAIEEFPVPALHHPVFQ

QESFTRQVLWKLLKVVKFGEVISYQQLAALAGNPAATAAVKTALSGNPVP

ILIPCHRVVSSSGAVGGYEGGLAVKEWLLAHEGHRLGKPGLGPAAIGAPG

SGSGSPAGCQQEGLVPEGGVEEERDHWQQFYFLSKRRRNLLRNPCGEEDL

EGWCDVEHGGDGWRVEELPGDSGVEFTHDESVKKYFASSFEWCRKAQVID

LQAEGYWEELLDTTQPAIVVKDWYSGRSDAGCLYELTVKLLSEHENVLAE

FSSGQVAVPQDSDGGGWMEISHTFTDYGPGVRFVRFEHGGQDSVYWKGWF

GARVTNSSVWVEP

The sequence in bold is a linker sequence. The sequence preceding the linker sequence is AGT variant (immobilization module). The sequence following the linker sequence is SEQ ID NO: 2 and could be a variant thereof.

(SEQ ID NO: 4)
MGSSHHHHHHGDKDCEMKRTTLDSPLGKLELSGCEQGLHEIKLLGKGTS

AADAVEVPAPAAVLGGPEPLMQATAWLNAYFHQPEAIEEFPVPALHHPV

FQQESFTRQVLWKLLKVVKFGEVISYQQLAALAGNPAATAAVKTALSGN

PVPILIPCHRVVSSSGAVGGYEGGLAVKEWLLAHEGHRLGKPGLGPA

SEQ ID NO: 4 is the immobilization module (AGT variant) as used for the fusion protein in SEQ ID NO: 3.

All references cited herein including U.S. application Ser. No. 15/320,911, filed Dec. 21, 2016; International Application No. PCT/US2015/37960 filed Jun. 26, 2015; and U.S. Provisional Ser. No. 62/020,335 filed Jul. 2, 2014 are incorporated by reference.

EXAMPLES

The following experiments refer to various buffers. These are as follows:

Trypsin digestion buffer: 50 mM ammonium bicarbonate.

The first buffer or binding buffer may be a high salt buffer, high salt volatile buffer, a low salt buffer or a low salt volatile buffer. Volatile buffers are preferred for mass spectrometry.

High salt buffer: 2 M NaCl, 20 mM Tris-HCl, 1 mM EDTA, pH 7.5;

High salt volatile buffer: 2 M ammonium acetate, pH 7.5 (for use in mass spectrometry);

Low salt buffer: 50 mM NaCl, 20 mM Tris-HCl, 1 mM EDTA, pH 7.5;

Low salt volatile buffer: 50 mM ammonium acetate, pH 7.5 (for use in mass spectrometry);

Dialysis buffer: may be the same as the first buffer;

The second buffer is 50% acetonitrile v/v in water.

Example 1: Enrichment of N-Glycan Linked Glycomolecules from a Complex Mixture (FIG. 1)

Protein or peptide based glycomolecules within a complex sample may be characterized using Fbs to accomplish enrichment of N-glycan linked glycopeptides. For example, the method may applied to biological samples such as serum, urine, cell lysates, or other body fluids. The complex mixture containing N-glycan linked glycoprotein, non-glycosylated protein and other biomolecules is first digested with a protease such as trypsin in 50 mM ammonium bicarbonate. The protease is optionally removed by filtration or other means such as immobilization. A protease inhibitor such as phenylmethanesulfonyl fluoride (PMSF) or trypsin inhibitor is added to inhibit proteolysis. The glycopeptide and peptide mixture is then incubated with Fbs immobilized on beads or immobilized on another surface in either a low salt or high salt buffer. While the N-glycan linked glycopeptides bind to immobilized Fbs, O-linked glycopeptides and non-glycosylated peptides or proteins will remain in solution. One or more washing steps are carried out to remove material that is not bound to immobilized Fbs. The wash buffer is typically the same as the buffer used for binding. The bound N-glycan linked glycopeptides are then eluted using a mass spectrometry (mass spec) friendly solvent such as 50% acetonitrile in water. The enriched sample is analyzed by mass spec (Nilsson, et al., *Nature Methods*, 6, 809-813 (2009)) to reveal the identity and relative quantity of N-glycan linked glycopeptides (see box labeled "after selection").

Example 2: Over-Expression of an Exemplary Binding Reagent and Immobilization to a Solid Support An example of a binding reagent shown in FIG. 1 is Fbs fused to the SNAP-tag protein. SNAP-tag substrates are derivatives of benzylpurines and benzylchloropyrimidines. In the conjugation reaction, the substituted benzyl group of the substrate is covalently attached to the SNAP-tag. SNAP-Fbs expresses at a high level as a soluble protein in *E. coli* using pSNAP-tag(T7)-2 vector (New England Biolabs, Ipswich, Mass.).

SNAP-Fbs is efficiently conjugated to BG beads (SNAP Capture Pull-Down resin (New England Biolabs, Ipswich, Mass.): SNAP-Fbs protein is reacted with BG beads at 4° C. overnight in a DTT-containing buffer (4 mM DTT, 20 mM tris-HCl pH 7.5, 1 mM EDTA, 50 mM NaCl). After the conjugation reaction, SNAP-Fbs beads are washed with 40× bead volume of low salt buffer.

Example 3: N-Glycan-Specific Binding by the Binding Reagent (FIG. 2A)

N-Glycan-specific binding of the binding reagent was demonstrated using RNase B. RNase B is a glycoprotein with an N-linked high mannose glycan. Thirty micrograms RNase B was denatured by boiling in 0.5% SDS and 40 mM DTT. After boiling, 1% NP-40 was added. The denatured RNase B was either untreated or treated with PNGase F (for 1 hour at 37° C. in 50 mM sodium phosphate, pH 7.5) to remove N-glycans. The untreated and treated samples were incubated with SNAP-Fbs conjugated to BG beads (SNAP-Capture Pull-Down resin) at 4° C. for 1 hour in low salt buffer. Fbs beads were centrifuged, then washed twice with the low salt buffer, and bound proteins on the beads were eluted in 1×SDS gel loading buffer (New England Biolabs, Ipswich, Mass.) and analyzed by SDS-PAGE. Lane 1 is control untreated RNase B containing N-glycan that was not exposed to Fbs beads. Lane 2 is an RNase B sample pre-treated with PNGase F and then incubated with Fbs beads. Thus N-linked glycoprotein is not bound and eluted. Lane 3 is untreated RNaseB which was bound and eluted from Fbs beads.

Example 4: The Binding Reagent Efficiently Binds to N-Glycan Linked Glycomolecules with Complex N-Glycans (FIG. 2B)

Efficient binding of the binding reagent to N-glycan linked glycomolecules with complex N-glycans was demonstrated using human IgG (Bethyl Laboratories, Montgomery, Tex.). Binding depends on the presence of the N-glycan. Human IgG is a glycoprotein with an N-linked glycan in the heavy chain (at Asn297) with complex glycan structure, and typically no N-linked glycans are present in the light chain. The same conditions described in Example 3 were used to assay 50 μg human IgG binding to Fbs. Lane 1 is a control showing the IgG without any treatment. Lanes 3 and 4 show that only the heavy chain is bound by Fbs beads and only when glycan is present (Lane 4). In lanes 2, 3 and 4, the asterisk indicates a small amount of SNAP-Fbs protein that is released from the beads during boiling in gel loading buffer to elute bound heavy chain. The light chain of IgG, on which there is no N-linked glycan, did not bind to Fbs beads. This is an example to show that Fbs binding is specific for N-linked glycoproteins or glycopeptides.

Example 5: The Binding Reagent is Unaffected by Fucosylation of the Core Pentasaccharide (FIG. 3)

Fbs binds to N-glycan and N-glycan with fucose modification at the reducing end of GlcNAc. Isothermal titration calorimetry was used to assay the interaction between Fbs and core structure glycans. Man3GlcNAc2 (M3N2) and Man3GlcNAc2 with (alpha 1-6) fucose modification at the reducing end of GlcNAc (M3N2F) were used as binding substrates (both substrates were purchased from Prozyme, Hayward, Calif. SNAP-Fbs was dialysed against low salt buffer and the glycans were also dissolved in the same dialysis buffer. A Nano ITC instrument (TA Instruments, Lindon, Utah) with 170 μl cell volume and 50 μl buret volume was used. Every 300 seconds, 2.97 μl of 90 μM glycan was automatically injected into 9 μM Fbs solution. The data was fitted using a single site binding model (Nanoanalyze software (TA Instruments, Lindon, Utah)), and the Kd was calculated. The affinity of Fbs for Man3GlcNAc2 (Kd M3N2=0.123±0.036 μM) is very similar to the affinity of Fbs for Man3GlcNAc2 modified with fucose (Kd M3N2F=0.128±0.037 μM) indicating that N-glycan binds to Fbs tightly and fucosylation of the first GlcNAc residue from the reducing end does not impair binding by Fbs.

Example 6: 2-AB Fluorophore Labeling at the Reducing End of M3N2 Abolishes Binding by Fbs (FIG. 4)

When PNGase F is used to trim N-glycans away from the peptides or proteins, the terminal GlcNAc residue becomes available for modification. A common modification is fluorophore labeling using 2-AB dye. The primary amino group of the dye performs a nucleophilic attack on the carbonyl carbon of the acyclic reducing terminal residue to form a partially stable Schiff's base. The Schiff's base imine group is chemically reduced to give a stable labeled glycan. The conserved terminal GlcNAc residue is thus referred to as the "reducing end" of a glycan species. Upon 2-AB labeling, the carbohydrate ring structure is no longer capable of forming. Fbs binding to 2-AB labeled M3N2 was tested and the results are shown in FIG. 4. Fifty picomoles of 2-AB labeled M3N2 in low salt buffer were incubated with SNAP-Fbs beads or SNAP control beads (SNAP Capture beads conjugated to SNAP-tag Purified Protein, New England Biolabs, Ipswich, Mass.). The majority of the 2-AB labeled fluorophore was found in the flow-through and low salt buffer wash fractions in both samples indicating that 2-AB labeling disrupts the interaction between glycan and Fbs. This consequence does not affect the application of Fbs for N-glycan linked glycomolecule enrichment as the 2-AB labeling step is an optional step downstream from the enrichment step.

Example 7: The Binding Reagent Effectively Binds Charged N-Glycans Containing Sialic Acids (FIG. 5)

Isothermal titration calorimetry analysis of SGP (Fushimi Pharmaceutical Co., Marugame, Japan) binding to SNAP-Fbs. SNAP-Fbs was dialysed against low salt buffer and SGP was also dissolved in the same low salt buffer. A Nano ITC instrument with 170 μl cell volume and 50 μl buret volume was used. Every 300 seconds, 2.97 μl of 270 μM SGP was automatically injected into 27 μM Fbs solution. The data was fitted using a single site binding model (Nanoanalyze software), and Kd was calculated. In low salt conditions, SNAP-Fbs binds a complex-type oligosaccharide chain with two terminal sialic acid residues with a Kd=3.0±0.12 μM.

Example 8: Binding to Charged N-Glycan Linked Glycomolecules by the Binding Reagent is Substantially Unbiased in High Salt Buffer (FIG. 6A)

Fbs binding to complex N-glycan linked glycomolecules is substantially unbiased in a high salt buffer. SGP was labeled with two tetramethylrhodamine (TMR) fluorophores on the peptide portion via lysine residues according to the TMR protein labeling kit protocol (Genaxxon Bioscience, Ulm Germany). After TMR labeling, a fraction of the SGP-TMR sample was processed with neuraminidase (New England Biolabs, Ipswich, Mass.) to remove terminal sialic acid residues. Two binding conditions (LS, low salt buffer and HS, high salt buffer) were tested. The presence of sialic acid residues significantly reduces binding in low salt conditions (compare column 1 vs. column 3) whereas binding of sialylated SGP and asialo-SGP is greater than 65% in both low salt and high salt buffer (see column 2 and column 4). TMR Fluorescence in the supernatant was measured using a SpectraMax M5 fluorometer (excitation 555 nm and emission 595 nm with 590 nm cutoff). Binding of SGP-TMR to Fbs (y-axis) is determined by subtracting the fluorescence measured in the bead supernatant from the input fluorescence.

Example 9: Binding of the Binding Reagent to Complex N-Glycan Linked Glycomolecules is Enhanced by Increasing the Ionic Strength of the Binding Buffer (FIGS. 6A-6C)

In FIG. 6B, sialylglycopeptide labeled with two pentamethylrhodamine (PMR) fluorophores on the peptide portion (via lysines), was used as an N-glycopeptide substrate for a binding assay with Fbs beads. SGP-TMR was dissolved in various solutions with increasing concentrations of ammonium acetate. Each sample was incubated with SNAP-Fbs beads for 20-30 minutes at 4° C. The % SGP-TMR bound to the beads was determined by measuring the fluorescence in the bead supernatant and then subtracting this value from the input fluorescence. TMR Fluorescence was measured using a SpectraMax M5 fluorometer (Molecular Devices, Sunnyvale, Calif.) (excitation 555 nm and emission 595 nm with 590 nm cutoff). Strikingly, binding of the Fbs to the complex N-glycan linked glycomolecule was enhanced by increasing the ionic strength of the binding solution in the range of 0 mM to 3000 mM ammonium acetate.

Example 10: High Salt Significantly Improves Binding of wtFbs to Complex N-Glycan Linked Glycomolecules (FIG. 6C)

Isothermal titration calorimetry was employed to analyze the binding of SNAP-wtFbs to SGP in solution. High salt buffer was tested as the common buffer for the binding reagent and the substrate SGP. Other conditions for the ITC experiment were the same as those listed in Example 7. The single change in NaCl concentration from 50 mM to 2000 mM resulted in a much greater affinity between wtFbs and SGP. The table in FIG. 6C shows that high salt conditions result in a Kd=1.43±0.12 µM which is more than a 2-fold higher affinity compared to 3.0±0.12 µM in low salt buffer.

Example 11: Immobilized Fbs Binding Reagent Facilitates Enrichment of N-Glycan Linked Glycomolecules from a Complex Sample (FIG. 7A)

Fbs beads were used to capture and enrich N-glycopeptides from a complex mixture. The complex mixture was a tryptic digest of RNase B spiked with SGP to serve as a complex, sialylated glycopeptide. RNase B contains several non-glycosylated peptides and several different high mannose N-glycopeptides (labeled in the enlargement as: M5N2, M6N2). One hundred eighty-five micrograms RNase B was digested with 4 micrograms trypsin (New England Biolabs, Ipswich, Mass.) in trypsin digestion buffer and then filtered with a 10 kDa Microcon 10 centrifugal filter unit (Millipore, Billerica, Mass.) to remove trypsin and any undigested RNase B. PMSF (1 mM final concentration) was added to inhibit any residual trypsin. 100 micrograms SGP was added to the RNase B digest. Then immobilized binding reagent, SNAP-Fbs beads in this example, was mixed with the complex mixture and incubated at 4° C. for 1 hour in the presence of either low salt volatile buffer or high salt volatile buffer. The beads were washed with low salt volatile buffer or high salt volatile buffer, respectively. The bound N-glycopeptides were eluted using 50% acetonitrile, then lyophilized and analyzed by mass spec (LC-MS method). The TIC and enlargement demonstrates wild type Fbs-mediated binding and enrichment of N-glycopeptides from a complex mixture. The dotted line indicates the chromatogram of the input mixture without enrichment. The solid black line indicates the chromatogram of the high salt enrichment sample (HS enrichment=2M ammonium acetate pH 7.5). The solid gray line indicates the chromatogram of the low salt enrichment sample (LS enrichment=50 mM ammonium acetate pH 7.5). The enlarged box focuses on the glycomolecules that elute between 20-22 minutes whereas the non-glycosylated peptides elute before 20 minutes. Strikingly, the non-glycosylated peptides were not enriched. Thus, N-glycopeptides present in the sample were selectively bound by the binding reagent when using LS or HS enrichment.

Example 12: Quantification of the Selective Binding of N-Glycopeptides from a Complex Mixture (FIG. 7B)

The different peptides and N-glycopeptides present in the complex mixture described in Example 11 were quantified. The extracted ion chromatogram results demonstrate that the binding reagent is selective for N-glycopeptides and does not capture non-glycosylated peptides from the complex mixture. Importantly, high salt volatile buffer improves the enrichment of SGP to the same level as non-sialylated M5N2 and M6N2. This demonstrates the universal ability of the wild-type Fbs binding reagent to bind all N-glycan linked glycomolecules in a substantially unbiased manner.

Example 13: Wild-Type Fbs Enrichment of a Diverse Set of N-Linked Glycopeptides is Substantially Unbiased in High Salt Volatile Buffer (FIG. 7C)

One hundred eighty micrograms human transferrin was digested with nine micrograms trypsin in 50 mM ammonium bicarbonate and then filtered with a 10 kDa Microcon 10 centrifugal filter unit to remove trypsin and any undigested transferrin. PMSF (1 mM final concentration) was added to inhibit any residual trypsin. The filter flow-through sample was adjusted to 2M ammonium acetate, pH 7.5 (high salt volatile buffer conditions) and then incubated with SNAP-Fbs beads for 60 minutes at 4° C. Then the sample was washed three times with high salt volatile buffer and then eluted with 50% acetonitrile (in water). The sample was lyophilized to remove residual bicarbonate, ammonium acetate, water and acetonitrile.

The sample was resuspended in PNGase F reaction buffer according to the New England Biolabs standard protocol. PNGaseF was added to release N-linked glycans from the digested glycopeptides. In this experiment N-glycans were released to reduce the complexity of the sample in order to allow highly accurate determination of each glycan species. N-glycans were labeled with 2-AB fluorophore (Prozyme, standard protocol) and analyzed by LC-MS. The composition of human transferrin is known by those skilled in the art so the glycans eluted in each peak can be inferred by using glycan standards. Mass analysis is also used to confirm the mass of each glycan type. When using high salt volatile buffer, the recovery of various types of complex N-linked glycomolecules was substantially unbiased within the range of 28.2 to 42.7%.

Example 14: N-Glycan Linked Glycomolecules are Reversibly Bound to Immobilized Binding Reagent and can be Readily Released (FIG. 8)

N-glycan linked glycomolecules reversibly binds to Fbs beads. Different reagents were tested for releasing bound N-linked glycopeptides from Fbs beads. 100 µl Fbs beads with bound SGP-TMR were collected, washed with 300 µl low salt binding buffer once, and divided into three aliquots (30 µl beads each aliquot). 100 ul of 2 M ammonium bicarbonate ($NH_4HCO_3$), 50% acetonitrile, or 1% acetic acid were added to Fbs beads with bound SGP-TMR to elute SGP-TMR. The beads were centrifuged and supernatants were collected. The solvent in the supernatant was removed by vacuum evaporation using a speedvac, and SGP-TMR was reconstituted in low salt buffer. SGP-levels were measured as described in Example 9. FIG. 11A shows that 50% acetonitrile readily released approximately 78% of SGP-TMR in the first 100 µl elution. 1% Acetic acid released approximately 65% of SGP-TMR. In contrast, less than 30% of bound N-glycan linked glycomolecules were released with 2 M ammonium bicarbonate.

Example 15: Isolation of Fbs Mutants that Possess Improved Affinity to Complex N-Linked Glycomolecules (FIG. 9A-9C)

Fetuin, which contains sialylated complex N-linked glycans, served as the complex N-linked glycomolecule in this example. Fetuin was conjugated to Affigel 15 resin (Bio-Rad, Hercules, Calif.), and then denatured by 6 M Guanidine HCL. After denaturation, the fetuin beads were washed with 50 bead volumes of low salt buffer to remove Guanidine HCL. This immobilized denatured Fetuin was used to screen Fbs mutants for improved affinity to complex N-linked glycomolecules in low salt conditions in a fetuin pull-down assay. In this assay, cell lysates containing the same amount of wild type or mutant Fbs protein were incubated with the same amount of fetuin beads at 4° C. for 1 hour. After incubation, the fetuin beads were washed three times with low salt buffer. The bound Fbs proteins were eluted by 1× gel loading buffer, and analyzed by SDS-PAGE. In the fetuin pull-down assay, the amount of Fbs mutant protein shown on the SDS-PAGE gel indicates the relative affinity of each Fbs mutant for binding to a complex N-linked glycomolecule. Fbs amino acid residue serine 155 was mutated to alanine to assess the effect on the interaction with complex N-linked glycomolecules. Mutation of Ser155 to alanine was expected to reduce the affinity of the interaction between Fbs and fetuin according to the published report of Tanaka et al. (Tanaka, et al. PNAS). Contrary to the expectation, the S155A mutant showed 1.5 times greater ability to be pulled down by immobilized fetuin. Further investigation revealed that Fbs mutant S155G shows 2.0-fold greater capacity to interact with fetuin as determined by the fetuin pull-down assay.

To expand the search for high affinity Fbs mutants, plasmid display (Speight, et al., *Chemistry & Biology*, 8, 951-965 (2001)) was used to isolate Fbs mutants from a mutant library prepared by saturation mutagenesis of positions D154, S155, G156, F173 and E174 of human Fbs. Four additional Fbs mutants (designated as PPG, PPS, PPR, and YR in the table FIG. 9A) were identified which possess higher affinity (up to 2.8 fold increase) to the complex N-linked glycans on Fetuin (FIG. 9B). The Fbs mutant containing combined S155G and YR mutations (S155G+YR, also termed as GYR) or PPR and YR mutations (PPR+YR, also termed as PPRYR) possess even higher affinity (up to 4.5 fold increase) against complex N-linked glycans on Fetuin (FIG. 9C).

Example 16: Fbs GYR and PPRYR Mutants Show Substantially Reduced Bias in Binding to all Types of N-Linked Glycomolecule (FIGS. 10A-10C)

WT Fbs preferably binds to high mannose N-glycan linked glycomolecules such as RNase B, and possesses far lower affinity to sialyated complex N-glycan linked glycomolecules such as Fetuin. Fbs GYR and PPRYR mutants show significantly improved affinity to Fetuin (FIG. 9A-9C). The same amount of wild-type Fbs, Fbs GYR mutant and PPRYR mutant proteins were conjugated to SNAP capture resin using the conditions described in Example 2 (FIG. 10B). Binding to RNase B with high mannose N-glycan and Fetuin with sialyated complex N-glycan linked glycomolecules was analyzed in a single experiment. A mixture of denatured Fetuin and RNase B (denatured by boiling for 10 minutes in the presence of 1× Rapid PNGase F buffer (New England Biolabs, Ipswich, Mass.) were pulled down by the immobilized Fbs beads conjugated with equal amount of WT, GYR or PPRYR Fbs proteins (FIGS. 10A and 10B). The bound fetuin and RNase B were eluted by 1× gel loading buffer, and analyzed by -PAGE/Coomassie blue staining. The amount of fetuin or RNase B on -PAGE gels were quantified using Image J. The ratio of Fetuin to RNase B (Fetuin/RNase B) is arbitrarily defined as 1 in the input (FIG. 10A, Lane 7 and 10C). In low salt volatile buffer conditions, wild-type Fbs pulled down a very small amount of Fetuin (FIG. 10A, Lane1), and the Fetuin/RNase B is only 0.29 (FIG. 10C), which indicates biased N-glycan linked glycomolecule binding. In contrast, in the same low salt volatile buffer conditions, the GYR and PPRYR mutants pulled down significantly more Fetuin (FIG. 10A, Lane 2 and 3) and the Fetuin/RNase B ration is very near to 1 (FIG. 10C), indicating substantially unbiased in N-glycan linked glycomolecule binding. In high salt volatile buffer wild-type Fbs pulled down more Fetuin (FIG. 10A, Lane 4) and the Fetuin/RNase B ratio is increased to 0.92 (FIG. 10C), which indicates high salt conditions help to reduce the bias in N-glycan linked glycomolecule binding to wild-type Fbs. This is consistent with the data shown in FIGS. 6A-C and 7A-C. For the GYR and PPRYR mutants, the high salt conditions are not necessary, since Fetuin and RNase B pulldown was not enhanced (FIG. 10A, Lane 5 and 6, and FIG. 10C). The asterisk (*) indicates some SNAP-Fbs leached from the prototype immobilized Fbs beads.

Example 17. GYR and PPRYR Show Enhanced Binding to a Glycopeptide with a Complex N-Glycan (SGP-TMR) (FIG. 11)

SGP-TMR affinity to the Fbs in low salt volatile buffer was analyzed by a pull-down assay using SNAP Capture Pull-Down resin conjugated with equal amounts of WT, GYR or PPRYR Fbs proteins (FIG. 10B). The data shown as a bar graph in FIG. 11 was generated using the same experimental procedure as described in example 8. As compared to WT Fbs, GYR and PPRYR mutants show 3-fold and 2-fold increased affinity to SGP-TMR, respectively.

Example 18. Enrichment of N-Linked Glycomolecules from a Solution by Application of Fbs Immobilized to a Solid Support, which is Compatible with Microfluidic Sample Processing In the previous examples, the utility of Fbs has been described in the context of a SNAP-Fbs fusion protein, which is designed for immobilization to benzyl guanine beads (SNAP Capture Pull-down resin). Fbs may also be employed alone or as a fusion to other protein immobilization modules. Fbs, an Fbs fusion protein or Fbs conjugated to another type of immobilization module may be immobilized to the appropriate solid support. For example, Fbs or an Fbs fusion protein may be immobilized within a channel of a microfluidic device designed for processing small sample volumes (picoliter to milliliter scale). In a microfluidic device, a liquid sample containing N-linked glycomolecules would be allowed to come into contact with immobilized Fbs. The N-linked glycomolecules of interest will bind and other molecules in the sample would be washed away. After a washing step(s), 50% acetonitrile or other mass-spec friendly reagent may be added to elute the N-linked glycomolecules of interest. A primary advantage of such a microfluidic device is the potential for automated sample processing in-line with automated analysis of the N-linked glycomolecules of interest.

Example 19. Enrichment of N-Linked Glycomolecules from a Solution by Mixing with Non-Immobilized Fbs Fbs or Fbs fusion protein may be expressed as a recombinant protein that is readily soluble in an aqueous solution and readily available for interaction with a sample containing N-linked glycomolecules in solution. Separation of the N-linked glycomolecules of interest bound to Fbs may be separated from the other molecules in the sample by several methods including filtration or binding of the complex of interest to a solid support via an immobilization module. In the case of filtration, the N-linked glycomolecules bound to Fbs may be captured on a filter membrane with a molecular weight cut-off of 20 kDa or larger. For example, the Fbs SBD is greater than 20 kDa and the SNAP-Fbs fusion protein is approximately 45 kDa. Therefore, N-linked glycomolecules bound to the Fbs SBD or to an Fbs fusion protein will not pass through the membrane and other molecules less than 20 kDa will pass through a membrane with a molecular weight cut-off of 20 kDa or larger. After a washing step(s), 50% acetonitrile or other mass spec friendly reagent may be added to elute the N-linked glycomolecules from Fbs. This approach is envisaged for samples that have been processed by protease to create N-linked glycopeptides and/or processed with PNGase F to release N-linked glycans. These 2 molecules types may be enriched and then be eluted through the membrane for isolation and analysis. This hypothetical application of Fbs for enrichment of N-linked glycomolecules is similar to the work of Deeb, et al. who used a method named "N-glyco FASP", whereby lectin-based enrichment was used to quantify N-linked glycoproteins in lymphoma cells (Deeb, et al., *Mol Cell Proteomics*, 1, 240-51 (2014)).

For all patents, applications, or other references cited herein, such as non-patent literature and reference sequence information (such as database or accession numbers) are incorporated by reference in its entirety for all purposes as well as for the proposition that is recited. Where any conflict exits between a document incorporated by reference and the present application, this application will control.

As will be recognized by the person having ordinary skill in the art following the teachings of the specification, the foregoing aspects can be claimed by Applicant in any combination or permutation. To the extent one or more elements and/or features is later discovered to be described in one or more references known to the person having ordinary skill in the art, they may be excluded from the claims by, inter alia, a negative proviso or disclaimer of the one or more elements and/or features. Headings used in this application are for convenience only and do not affect the interpretation of this application or claims.

What is claimed is:

1. A protein comprising a non-naturally occurring amino acid sequence having at least 95% sequence identity to SEQ ID NO: 2 and mutations at least at two positions selected from positions that correspond to positions 42, 43, 44, 61, and 62 in SEQ ID NO:2.

2. The protein according to claim 1, comprising an immobilization module to form a fusion protein.

3. The protein according to claim 1, wherein the position of at least one of the at least two mutations are selected from positions corresponding to amino acid 43, 61, and 62.

4. The protein according to claim 1, wherein the mutations at least at two positions are selected from a Proline (P) at a position corresponding to amino acid 42, an Alanine (A), Glycine (G) or Proline (P) at a position corresponding to amino acid 43, a Serine (S) or Arginine (R) at a position corresponding to amino acid 44, a Tyrosine (Y) at a position corresponding to amino acid 61 or an Arginine (R) at a position corresponding to amino acid 62.

5. The protein according to claim 3, wherein the position of at least one of the at least two mutations are selected from positions corresponding to Alanine (A), Glycine (G) or Proline (P) at a position corresponding to amino acid 43, a Tyrosine (Y) at a position corresponding to amino acid 61 and an Arginine (R) at a position corresponding to amino acid 62.

6. The fusion protein according to claim 2, wherein the immobilization module is a variant of $O^6$-alkylguanine-DNA alkyltransferase (AGT).

7. The protein according to claim 4, fused to an immobilization module.

8. The protein according to claim 7, wherein the immobilization module is a variant of $O^6$-alkylguanine-DNA alkyltransferase (AGT).

* * * * *

SEQUENCE LISTING

```
<160> NUMBER OF SEQ ID NOS: 4

<210> SEQ ID NO 1
<211> LENGTH: 184
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: 0
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
```

```
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (48)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (88)..(91)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (103)..(104)
<223> OTHER INFORMATION: Xaa can be any naturally occurring amino acid
<220> FEATURE:
<221> NAME/KEY: misc_feature
<222> LOCATION: (108)..(108)
```

```
<223> OTHER INFORMATION: Xaa can be any naturally occurring amino acid
<220> FEATURE:
<221> NAME/KEY: misc_feature
<222> LOCATION: (114)..(115)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (122)..(127)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (131)..(137)
<223> OTHER INFORMATION: Xaa can be any naturally occurring amino acid
<220> FEATURE:
<221> NAME/KEY: misc_feature
<222> LOCATION: (139)..(140)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (146)..(147)
<223> OTHER INFORMATION: Xaa can be any naturally occurring amino acid
<220> FEATURE:
<221> NAME/KEY: misc_feature
<222> LOCATION: (154)..(155)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (164)..(166)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid

<400> SEQUENCE: 1

Phe Tyr Phe Leu Ser Lys Arg Arg Arg Asn Leu Xaa Xaa Asn Xaa Cys
1               5                   10                  15

Gly Xaa Xaa Xaa Leu Xaa Xaa Trp Xaa Xaa Val Glu Xaa Gly Gly Asp
            20                  25                  30

Gly Trp Xaa Xaa Glu Xaa Leu Pro Gly Asp Xaa Gly Xaa Xaa Phe Xaa
```

```
                35                  40                  45
Xaa Xaa Xaa Xaa Val Xaa Lys Xaa Phe Xaa Xaa Ser Xaa Glu Trp Cys
        50                  55                  60

Arg Lys Xaa Gln Xaa Xaa Asp Leu Xaa Ala Glu Gly Tyr Trp Glu Glu
65                  70                  75                  80

Leu Leu Asp Xaa Xaa Gln Pro Xaa Xaa Xaa Lys Asp Trp Tyr Xaa
                85                  90                  95

Gly Arg Xaa Asp Ala Gly Xaa Xaa Tyr Glu Leu Xaa Val Lys Leu Leu
            100                 105                 110

Ser Xaa Xaa Glu Xaa Val Leu Ala Glu Xaa Xaa Xaa Xaa Xaa Ala
        115                 120                 125

Xaa Pro Xaa Xaa Xaa Xaa Xaa Xaa Trp Xaa Xaa Ile Ser Xaa Thr
        130                 135                 140

Phe Xaa Xaa Tyr Gly Pro Gly Val Arg Xaa Xaa Arg Phe Xaa His Xaa
145                 150                 155                 160

Gly Gln Asp Xaa Xaa Xaa Trp Lys Gly Trp Xaa Gly Xaa Arg Xaa Thr
            165                 170                 175

Asn Ser Ser Val Xaa Val Xaa Pro
            180
```

<210> SEQ ID NO 2
<211> LENGTH: 184
<212> TYPE: PRT
<213> ORGANISM: Artificial Sequence
<220> FEATURE:
<223> OTHER INFORMATION: Synthetic construct

<400> SEQUENCE: 2

```
Phe Tyr Phe Leu Ser Lys Arg Arg Asn Leu Leu Arg Asn Pro Cys
1               5                   10                  15

Gly Glu Glu Asp Leu Glu Gly Trp Cys Asp Val Glu His Gly Gly Asp
                20                  25                  30

Gly Trp Arg Val Glu Glu Leu Pro Gly Asp Ser Gly Val Glu Phe Thr
            35                  40                  45

His Asp Glu Ser Val Lys Lys Tyr Phe Ala Ser Ser Phe Glu Trp Cys
50                  55                  60

Arg Lys Ala Gln Val Ile Asp Leu Gln Ala Glu Gly Tyr Trp Glu Glu
65                  70                  75                  80

Leu Leu Asp Thr Thr Gln Pro Ala Ile Val Val Lys Asp Trp Tyr Ser
                85                  90                  95

Gly Arg Ser Asp Ala Gly Cys Leu Tyr Glu Leu Thr Val Lys Leu Leu
            100                 105                 110

Ser Glu His Glu Asn Val Leu Ala Glu Phe Ser Ser Gly Gln Val Ala
        115                 120                 125

Val Pro Gln Asp Ser Asp Gly Gly Trp Met Glu Ile Ser His Thr
        130                 135                 140

Phe Thr Asp Tyr Gly Pro Gly Val Arg Phe Val Arg Phe Glu His Gly
145                 150                 155                 160

Gly Gln Asp Ser Val Tyr Trp Lys Gly Trp Phe Gly Ala Arg Val Thr
            165                 170                 175

Asn Ser Ser Val Trp Val Glu Pro
            180
```

<210> SEQ ID NO 3
<211> LENGTH: 413
<212> TYPE: PRT

<213> ORGANISM: Artificial Sequence
<220> FEATURE:
<223> OTHER INFORMATION: Synthetic construct

<400> SEQUENCE: 3

```
Met Gly Ser Ser His His His His His Gly Asp Lys Asp Cys Glu
1               5                   10                  15

Met Lys Arg Thr Thr Leu Asp Ser Pro Leu Gly Lys Leu Glu Leu Ser
            20                  25                  30

Gly Cys Glu Gln Gly Leu His Glu Ile Lys Leu Leu Lys Gly Thr
            35                  40                  45

Ser Ala Ala Asp Ala Val Glu Val Pro Ala Pro Ala Ala Val Leu Gly
50                  55                  60

Gly Pro Glu Pro Leu Met Gln Ala Thr Ala Trp Leu Asn Ala Tyr Phe
65                  70                  75                  80

His Gln Pro Glu Ala Ile Glu Gly Phe Pro Val Pro Ala Leu His His
                85                  90                  95

Pro Val Phe Gln Gln Glu Ser Phe Thr Arg Gln Val Leu Trp Lys Leu
                100                 105                 110

Leu Lys Val Val Lys Phe Gly Glu Val Ile Ser Tyr Gln Gln Leu Ala
            115                 120                 125

Ala Leu Ala Gly Asn Pro Ala Ala Thr Ala Ala Val Lys Thr Ala Leu
            130                 135                 140

Ser Gly Asn Pro Val Pro Ile Leu Ile Pro Cys His Arg Val Val Ser
145                 150                 155                 160

Ser Ser Gly Ala Val Gly Gly Tyr Glu Gly Gly Leu Ala Val Lys Glu
                165                 170                 175

Trp Leu Leu Ala His Glu Gly His Arg Leu Gly Lys Pro Gly Leu Gly
                180                 185                 190

Pro Ala Ala Ile Gly Ala Pro Gly Ser Gly Ser Gly Ser Pro Ala Gly
            195                 200                 205

Cys Gln Gln Glu Gly Leu Val Pro Glu Gly Gly Val Glu Glu Glu Arg
            210                 215                 220

Asp His Trp Gln Gln Phe Tyr Phe Leu Ser Lys Arg Arg Arg Asn Leu
225                 230                 235                 240

Leu Arg Asn Pro Cys Gly Glu Glu Asp Leu Glu Gly Trp Cys Asp Val
                245                 250                 255

Glu His Gly Gly Asp Gly Trp Arg Val Glu Glu Leu Pro Gly Asp Ser
                260                 265                 270

Gly Val Glu Phe Thr His Asp Glu Ser Val Lys Lys Tyr Phe Ala Ser
            275                 280                 285

Ser Phe Glu Trp Cys Arg Lys Ala Gln Val Ile Asp Leu Gln Ala Glu
290                 295                 300

Gly Tyr Trp Glu Glu Leu Leu Asp Thr Thr Gln Pro Ala Ile Val Val
305                 310                 315                 320

Lys Asp Trp Tyr Ser Gly Arg Ser Asp Ala Gly Cys Leu Tyr Glu Leu
                325                 330                 335

Thr Val Lys Leu Leu Ser Glu His Glu Asn Val Leu Ala Glu Phe Ser
                340                 345                 350

Ser Gly Gln Val Ala Val Pro Gln Asp Ser Asp Gly Gly Trp Met
            355                 360                 365

Glu Ile Ser His Thr Phe Thr Asp Tyr Gly Pro Gly Val Arg Phe Val
            370                 375                 380

Arg Phe Glu His Gly Gly Gln Asp Ser Val Tyr Trp Lys Gly Trp Phe
```

```
                385                 390                 395                 400
Gly Ala Arg Val Thr Asn Ser Ser Val Trp Val Glu Pro
                    405                 410

<210> SEQ ID NO 4
<211> LENGTH: 194
<212> TYPE: PRT
<213> ORGANISM: Artificial Sequence
<220> FEATURE:
<223> OTHER INFORMATION: Syntheitic construct

<400> SEQUENCE: 4

Met Gly Ser Ser His His His His His Gly Asp Lys Asp Cys Glu
 1               5                  10                  15

Met Lys Arg Thr Thr Leu Asp Ser Pro Leu Gly Lys Leu Glu Leu Ser
                20                  25                  30

Gly Cys Glu Gln Gly Leu His Glu Ile Lys Leu Leu Gly Lys Gly Thr
            35                  40                  45

Ser Ala Ala Asp Ala Val Glu Val Pro Ala Pro Ala Ala Val Leu Gly
        50                  55                  60

Gly Pro Glu Pro Leu Met Gln Ala Thr Ala Trp Leu Asn Ala Tyr Phe
65                  70                  75                  80

His Gln Pro Glu Ala Ile Glu Glu Phe Pro Val Pro Ala Leu His His
                85                  90                  95

Pro Val Phe Gln Gln Glu Ser Phe Thr Arg Gln Val Leu Trp Lys Leu
                100                 105                 110

Leu Lys Val Val Lys Phe Gly Glu Val Ile Ser Tyr Gln Gln Leu Ala
            115                 120                 125

Ala Leu Ala Gly Asn Pro Ala Ala Thr Ala Ala Val Lys Thr Ala Leu
        130                 135                 140

Ser Gly Asn Pro Val Pro Ile Leu Ile Pro Cys His Arg Val Val Ser
145                 150                 155                 160

Ser Ser Gly Ala Val Gly Gly Tyr Glu Gly Gly Leu Ala Val Lys Glu
                165                 170                 175

Trp Leu Leu Ala His Glu Gly His Arg Leu Gly Lys Pro Gly Leu Gly
                180                 185                 190

Pro Ala
```